US008961451B2

(12) United States Patent
Stearns et al.

(10) Patent No.: US 8,961,451 B2
(45) Date of Patent: Feb. 24, 2015

(54) SYSTEM FOR SURGICAL INSUFFLATION AND GAS RECIRCULATION

(75) Inventors: Ralph Stearns, Bozrah, CT (US); Kurt Azarbarzin, Fairfield, CT (US); Timothy J. Nolan, South Salem, NY (US)

(73) Assignee: SurgiQuest, Inc., Milford, CT (US)

( * ) Notice: Subject to any disclaimer, the term of this patent is extended or adjusted under 35 U.S.C. 154(b) by 23 days.

(21) Appl. No.: 11/960,701

(22) Filed: Dec. 20, 2007

(65) Prior Publication Data
US 2009/0137943 A1 May 28, 2009

Related U.S. Application Data

(63) Continuation of application No. PCT/US2007/088017, filed on Dec. 18, 2007.

(60) Provisional application No. 60/875,436, filed on Dec. 18, 2006, provisional application No. 60/923,917, filed on Apr. 17, 2007, provisional application No. 60/959,826, filed on Jul. 16, 2007.

(51) Int. Cl.
*A61M 37/00* (2006.01)
*A61B 17/34* (2006.01)
*A61M 13/00* (2006.01)

(52) U.S. Cl.
CPC .......... *A61B 17/3498* (2013.01); *A61B 17/3421* (2013.01); *A61B 17/3474* (2013.01);
(Continued)

(58) Field of Classification Search
CPC ........... A61B 17/3421; A61B 17/3462; A61B 17/3474; A61B 17/3498; A61M 13/003; A61M 2013/006; A61M 2205/3337

USPC ........... 600/560; 604/131, 140, 147, 151, 23, 604/26, 264, 27, 30, 31, 48, 93.01, 33, 65, 604/67, 164.01
See application file for complete search history.

(56) References Cited

U.S. PATENT DOCUMENTS 4,735,603 A 4/1988 Goodson et al.
5,098,387 A * 3/1992 Wiest et al. ............... 604/153
(Continued)

FOREIGN PATENT DOCUMENTS

WO WO 98/19736 A 4/1988
WO WO 02/085444 A 10/2002

OTHER PUBLICATIONS

International Search Report and Written Opinion mailed Mar. 9, 2009, issued in PCT Application No. PCT/US2007/088017.

*Primary Examiner* — Kami A Bosworth
*Assistant Examiner* — Imani Hayman
(74) *Attorney, Agent, or Firm* — Edwards Wildman Palmer LLP; Scott D. Wofsy

(57) ABSTRACT

A system for insufflation and recirculation of insufflation fluid in a surgical procedure. The system includes a control unit having a fluid pump, a supply conduit, a return fluid conduit and a pressure-controlled valve. The fluid pump is adapted and configured to circulate insufflation fluid through the system. The supply conduit is in fluid communication with an output of the fluid pump and configured and adapted for delivering pressurized insufflation fluid to an output port of the control unit. The return conduit is in fluid communication with an input of the fluid pump for delivering insufflation fluid to the fluid pump and is configured and adapted for returning insufflation fluid from an input port of the control unit. The pressure-controlled valve is in fluid communication with the supply conduit and the return conduit, and is adapted and configured to receive a control signal and respond to the control signal by opening, thereby fluidly connecting the supply conduit and the return conduit with one another.

10 Claims, 25 Drawing Sheets

(52) U.S. Cl.
CPC .......... *A61M13/003* (2013.01); *A61M 13/006* (2014.02); *A61B 17/3462* (2013.01); *A61M 2205/3337* (2013.01); *A61M 2205/3344* (2013.01)
USPC .............................. 604/26; 604/33; 604/67

(56) References Cited

U.S. PATENT DOCUMENTS

| | | | | |
|---|---|---|---|---|
| 5,246,419 A | * | 9/1993 | Absten | 604/26 |
| 5,360,396 A | * | 11/1994 | Chan | 604/26 |
| 5,429,483 A | | 7/1995 | Tamari | |
| 5,466,229 A | * | 11/1995 | Elson et al. | 604/317 |
| 5,556,386 A | * | 9/1996 | Todd | 604/247 |
| 6,302,873 B1 | | 10/2001 | Moenning | |
| 6,402,714 B1 | * | 6/2002 | Kraft-Kivikoski | 604/23 |
| 2004/0034339 A1 | | 2/2004 | Stoller et al. | |
| 2004/0204671 A1 | | 10/2004 | Stubbs et al. | |
| 2005/0004512 A1 | | 1/2005 | Campbell et al. | |
| 2005/0015043 A1 | * | 1/2005 | Stubbs et al. | 604/26 |
| 2006/0182637 A1 | | 8/2006 | Jacobsen et al. | |
| 2007/0088275 A1 | | 4/2007 | Stearns et al. | |

* cited by examiner

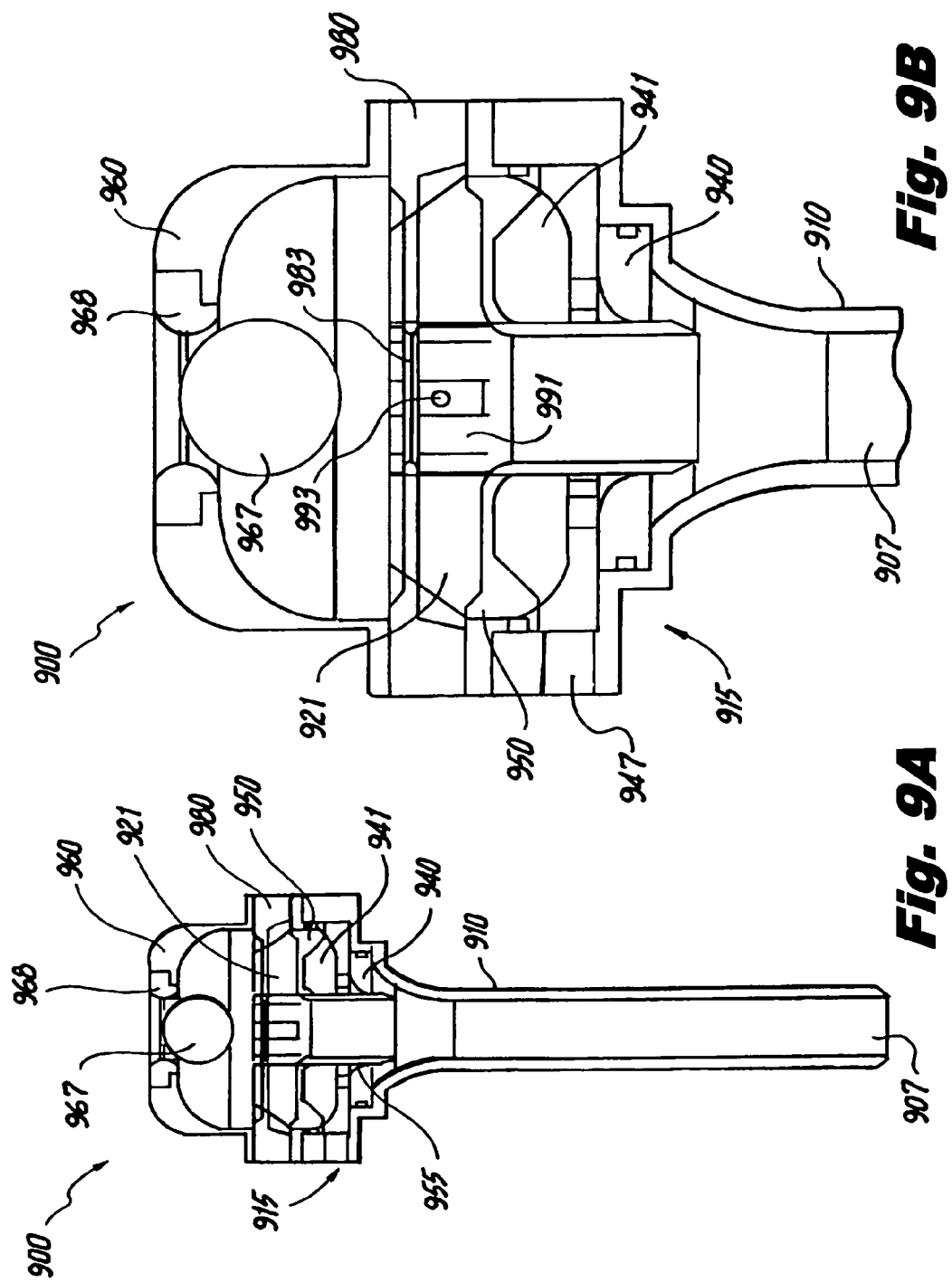

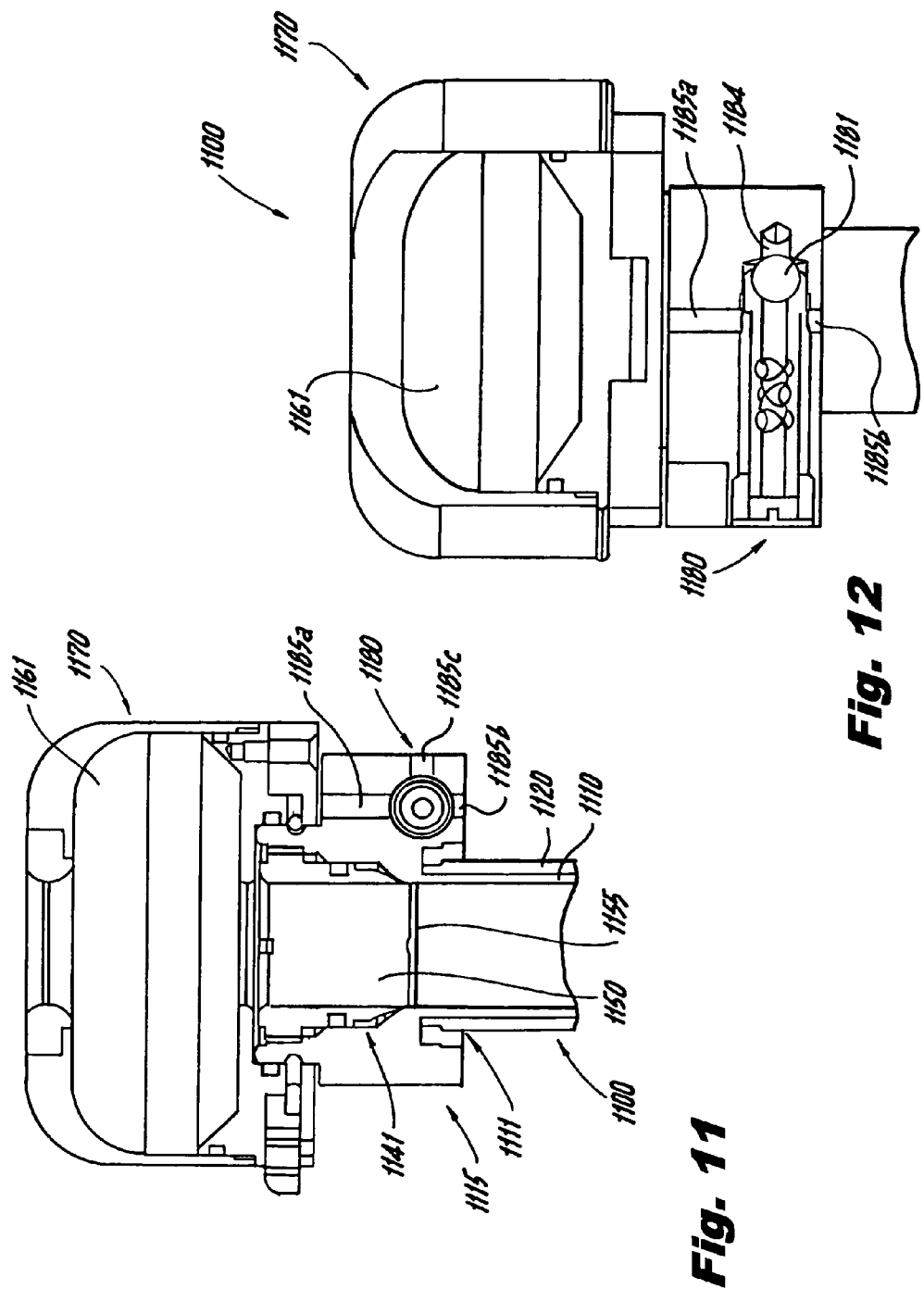

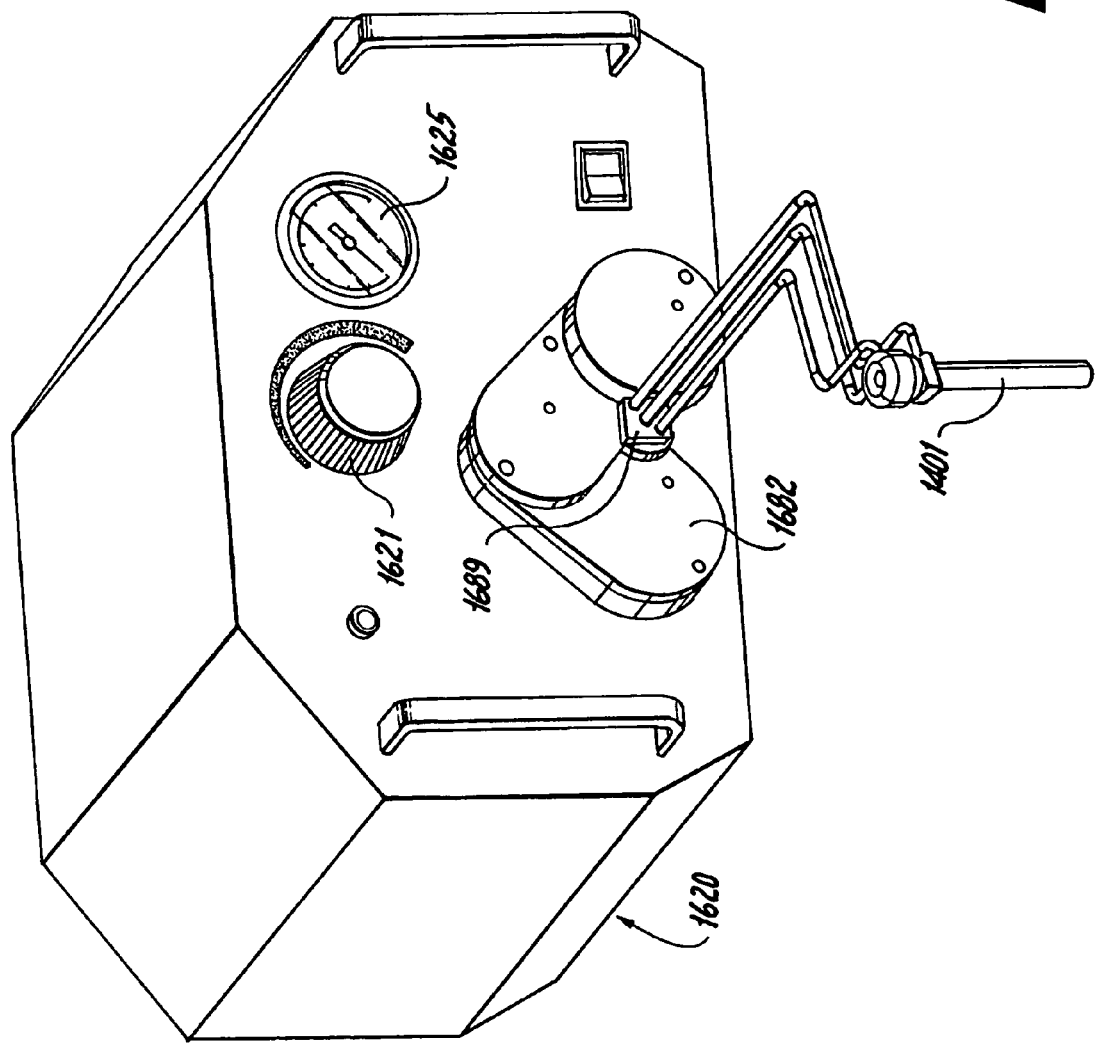

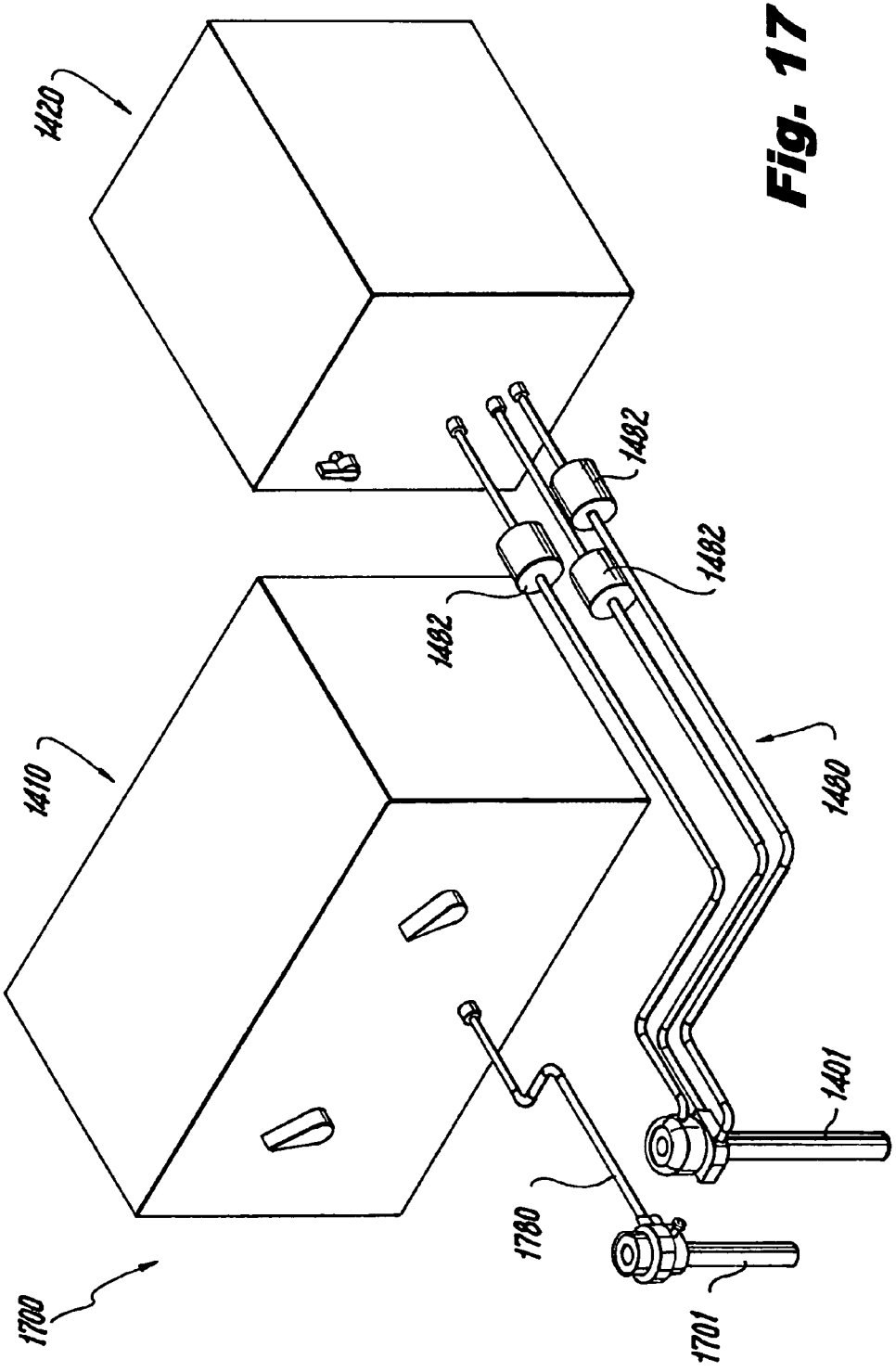

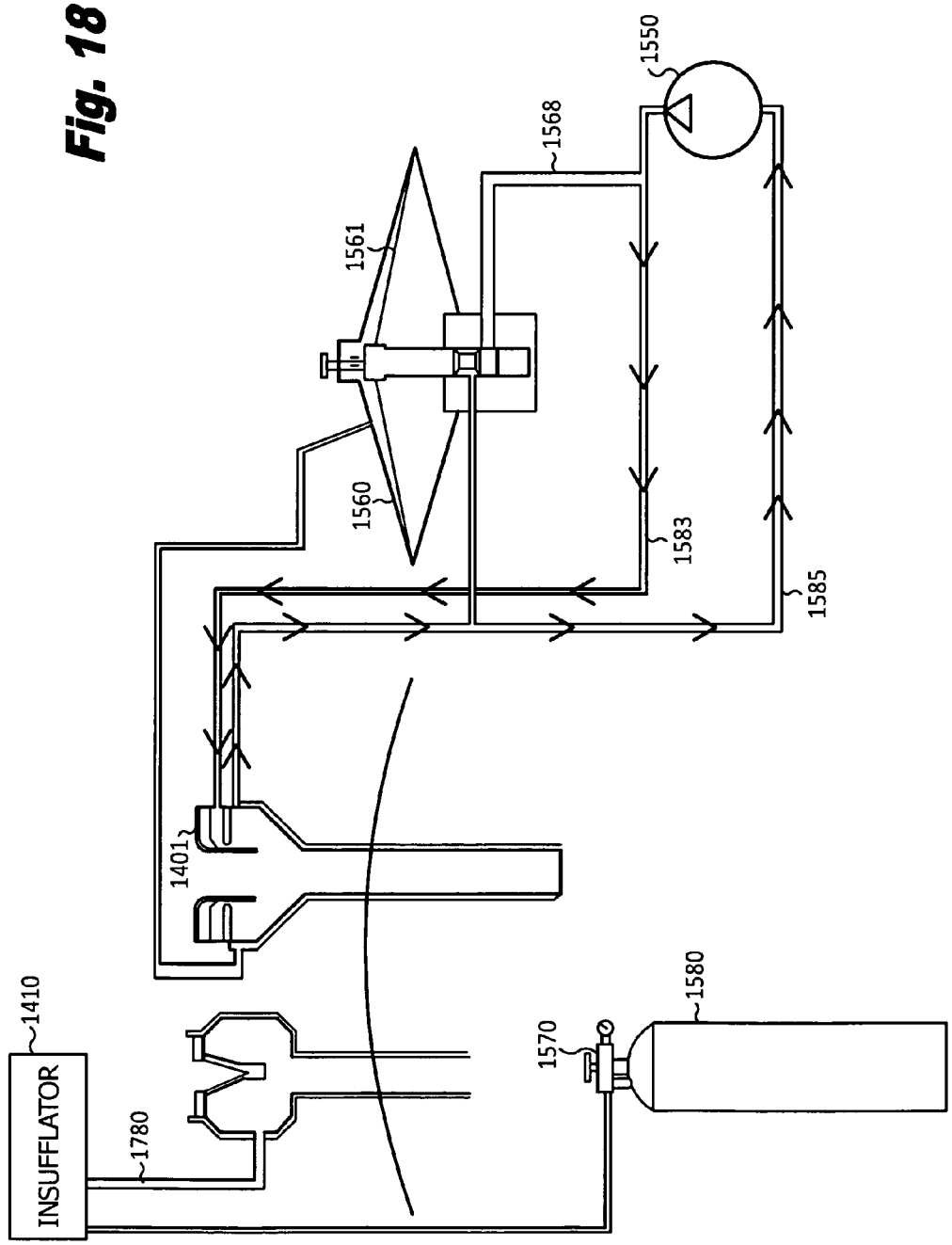

SYSTEM FOR SURGICAL INSUFFLATION AND GAS RECIRCULATION

CROSS-REFERENCE TO RELATED APPLICATIONS

This application is a continuation application of PCT application PCT/US07/88017 filed Dec. 18, 2007, which claims priority to U.S. Provisional Application No. 60/875,436 filed Dec. 18, 2006, U.S. Provisional Application No. 60/923,917 filed Apr. 17, 2007, and U.S. Provisional Application No. 60/959,826 filed Jul. 16, 2007. Each of the foregoing applications is hereby incorporated by reference in its entirety.

BACKGROUND OF THE INVENTION

1. Field of the Invention

The present application relates to systems and devices for surgical access, and is particularly directed devices adapted and configured to create a fluidic seal, and to systems for supplying pressurized fluid to such devices, which are also capable of recirculating such pressurized fluid. Surgical access devices configured for creating a fluidic seal for surgical access are set forth in the following applications, which are incorporated herein by reference in their entirety: U.S. patent application Ser. No. 11/517,929, filed Sep. 8, 2006, U.S. patent application Ser. No. 10/776,923, filed Feb. 11, 2004, U.S. patent application Ser. No. 10/739,872, filed Dec. 18, 2003, U.S. patent application Ser. No. 10/441,149, filed May 17, 2003, and U.S. Provisional Application Ser. No. 60/461,149, filed Apr. 8, 2003.

2. Description of Related Art

Laparoscopic, or "minimally invasive" surgical techniques are becoming increasingly more common. Benefits of such procedures include reduced trauma to the patient, reduced opportunity for infection, and decreased recovery time. Such procedures within the abdominal cavity are typically performed through a device known as a trocar or cannula, which facilitates the introduction of laparoscopic instruments into the abdominal cavity of a patient.

Additionally, such procedures commonly involve filling or "insufflating" the abdominal (peritoneal) cavity with a pressurized fluid, such as carbon dioxide, to create what is referred to as a pneumoperitoneum. The insufflation can be carried out by a trocar equipped to deliver insufflation fluid, or by a separate insufflation device, such as an insufflation needle. Introduction of surgical instruments into the pneumoperitoneum without a substantial loss of insufflation gas is desirable, in order to maintain the pneumoperitoneum.

During typical laparoscopic procedures, a surgeon makes three to four small incisions, usually no larger than about twelve millimeters each, which are typically made with the trocar devices themselves, typically using a separate inserter or obturator placed therein. Following insertion, the inserter is removed, and the trocar allows access for instruments to be inserted into the abdominal cavity. Typical trocars often provide means to insufflate the abdominal cavity, so that the surgeon has an open interior space in which to work.

The trocar must provide a means to maintain the pressure within the cavity by sealing between the trocar and the surgical instrument being used, while still allowing at least a minimum freedom of movement of the surgical instruments. Such instruments can include, for example, scissors, grasping instruments, occluding instruments, cauterizing units, cameras, light sources and other surgical instruments. Sealing elements or mechanisms are typically provided on trocars to prevent the escape of insufflation gas. Sealing elements or mechanisms typically include a duckbill-type valve made of a relatively pliable material, to seal around an outer surface of surgical instruments passing through the trocar. However, sealing in this manner is not usually complete, such seals cannot seal between multiple instruments, and such seals also inhibit free movement of the surgical instruments and/or removal of tissue through the trocar. Such seals are also vulnerable to damage during the surgical procedure. Alternatively, a flapper valve or spring-loaded trap door can be used. However, these types of mechanical valves suffer from similar drawbacks.

Most valves, and particularly duckbill-type valves, which include resilient valve members that directly contact surgical instruments, not only interfere with the movement of surgical instruments, but reduce the ability of a surgeon to accurately sense the patient anatomy on which the surgeon is operating. Minimally invasive surgical procedures are carried out with a visualization aid such as a camera, and as a result, depth perception on the part of the surgeon is inhibited. Moreover, when the endoscope passes through mechanical seals, lenses thereof can be dirtied, typically with smears appearing, resulting in further vision difficulty. The absence of mechanical seals also allows swabs and specimens to be extracted without excessive interference. Additionally, the ability to physically sense resistance of structures and of tissues through movement of the surgical instruments plays an important role in a successful and safe surgical procedure. Frictional forces imparted on surgical instruments by contact of the aforementioned mechanical valves can mask the sensory signals, i.e., the haptic perception, that the surgeon might otherwise use to determine precisely what is occurring at the opposite end of the surgical instruments being used. Accordingly, improvements to sealing technologies that allow unencumbered access while maintaining a pneumoperitoneum, are desired. The present invention provides a solution for these problems.

SUMMARY OF THE INVENTION

The purpose and advantages of the present invention will be set forth in and apparent from the description that follows. Additional advantages of the invention will be realized and attained by the devices, systems and methods particularly pointed out in the written description and claims hereof, as well as from the appended drawings.

To achieve these and other advantages and in accordance with the purpose of the invention, as embodied, the invention includes, in one embodiment, a system for insufflation and recirculation of insufflation fluid. The system includes a control unit having a fluid pump, a supply conduit, a return fluid conduit and a pressure-controlled valve. The fluid pump is adapted and configured to circulate insufflation fluid through the system. The supply conduit is in fluid communication with an output of the fluid pump and configured and adapted for delivering pressurized insufflation fluid to an output port of the control unit. The return conduit is in fluid communication with an input of the fluid pump for delivering insufflation fluid to the fluid pump and is configured and adapted for returning insufflation fluid from an input port of the control unit. The pressure-controlled valve is in fluid communication with the supply conduit and the return conduit, and is adapted and configured to receive a control signal and respond to the control signal by opening, thereby fluidly connecting the supply conduit and the return conduit with one another.

In absence of a control signal, the pressure-controlled valve can be configured to remain in a closed state. The pressure-controlled valve can be additionally in fluid communication with a pressure sensing conduit, and adapted and configured for communicating a pressure value at a distal end thereof to the pressure-controlled valve. The pressure-controlled valve can be a mechanical diaphragm valve, with the pressure sensing conduit in fluid communication with a pressure sensing chamber of the pressure-controlled valve. Alternatively, pressure sensing can be accomplished by way of an electronic pressure transducer electrically coupled to an electromechanical valve.

The system can further include a trocar having an elongated body defining a lumen therein, a nozzle operatively associated with the body for directing pressurized fluid into the lumen, and a fluid return plenum adapted and configured to collect spent insufflation fluid. A nozzle supply port is in fluid communication with the nozzle, for delivering a pressurized flow of insufflation fluid to the nozzle, and adapted and configured to receive pressurized insufflation fluid from an output port of the control unit. A fluid return port is in fluid communication with the fluid return plenum, and is adapted and configured for returning insufflation fluid from the trocar to an input port of the control unit. The trocar can further include a pressure sensing chamber adapted and configured to be in fluid communication with a patient's abdominal cavity and with the pressure-controlled valve of the control unit.

Systems in accordance with the invention can further include a connection kit having a plurality of connecting conduits, one or more filters, and one or more connectors. The plurality of connecting conduits are adapted and configured to connect the nozzle supply port of the trocar to the output port of the control unit, to connect the fluid return port of the trocar to the input port of the control unit, and to connect the pressure sensing chamber of the trocar to the pressure-controlled valve of the control unit. The filter element is provided in fluid communication with at least one of the connecting conduits. The one or more connectors are disposed at each end of the connecting conduits, and are configured and adapted to mutually engage the connection kit with the trocar at one end, and with the control unit at its opposite end.

The system can include a surgical insufflator adapted and configured to receive, through an input port thereof, a supply of insufflation gas from a source, an output port of the insufflator being in fluid communication with a pressure sensor for operating the pressure-controlled valve and with a patient's abdominal cavity, the insufflator being adapted and configured to sense pressure within the abdominal cavity and to provide insufflation fluid thereto.

The control unit can include the surgical insufflator incorporated into a single housing. Moreover, systems in accordance with the invention can further include first and second trocars. The first trocar can include an elongated body defining a lumen therein, a nozzle operatively associated with the body for directing pressurized fluid into the lumen to form a fluid seal thereacross, a fluid return plenum adapted and configured to collect spent insufflation fluid, a nozzle supply port in fluid communication with the nozzle, for delivering a pressurized flow of insufflation fluid to the nozzle, adapted and configured to receive pressurized insufflation fluid from an output port of the control unit, and a fluid return port in fluid communication with the fluid return plenum, adapted and configured for returning insufflation fluid from the trocar to an input port of the control unit. The second trocar can be in fluid communication with a surgical insufflator adapted and configured to receive, through an input port thereof, a supply of insufflation gas from a source, the insufflator being adapted and configured to sense pressure within an abdominal cavity and to deliver pressurized insufflation fluid thereto through the second trocar. The second trocar can be used as a primary trocar for insufflation of the abdomen prior to activation of the first trocar, or vice versa, as desired.

In accordance with the invention, the insufflator and the pressure-controlled valve can each be independently in fluid communication with a patient's abdominal cavity, and each are adapted and configured to sense abdominal pressure therein.

In accordance with a further aspect of the invention a trocar for use in a minimally-invasive surgical procedure is provided. The trocar includes an elongated body, a fluid supply plenum, a supply port, a nozzle and a fluid return port. The body defines a lumen therein, the proximal end portion of the body defining a housing, and a fluid supply plenum is defined in the housing. The supply port is in fluid communication with the fluid supply plenum, and is adapted and configured to receive pressurized insufflation fluid from a recirculation device and to deliver the pressurized insufflation fluid to the fluid supply plenum. The nozzle is in fluid communication with the fluid supply plenum and the lumen, and is configured and adapted for directing pressurized fluid into the lumen. The fluid return plenum is defined in the housing and arranged distal the fluid supply plenum. The fluid return plenum is adapted and configured to collect spent insufflation fluid. The fluid return port is in fluid communication with the fluid return plenum, and is adapted and configured for returning insufflation fluid from the trocar to a recirculation device.

The trocar can further include sound attenuation elements arranged in the fluid return plenum. The sound attenuation elements can be selected from the group consisting essentially of baffles and sound-absorbing material, such as foam, for example. The trocar can further include sound attenuation elements arranged in a proximal sound attenuation chamber arranged proximal to the fluid supply plenum.

In accordance with the invention, the fluid return plenum can be defined between a distal end of the housing and a first substantially annular insert placed in the housing, and the fluid supply plenum can be defined between the annular insert and a second substantially annular insert. The second substantially annular insert can have a substantially tubular member extending distally therefrom, with the nozzle being defined between the substantially tubular member and an central portion of the first substantially annular insert.

The trocar can further include a pressure sensing chamber adapted and configured to be placed in fluid communication with a patient's abdominal cavity. The pressure sensing chamber can be in fluid communication with a pressure sensing port defined on the trocar, for connecting to a pressure sensing element, such as a diaphragm or electronic pressure transducer, for example.

In accordance with another embodiment of the invention, a trocar for use in a minimally-invasive surgical procedure includes an elongated body and first, second, third and fourth inserts. The proximal end portion of the body defines a housing. The first insert has a substantially tubular configuration extending through the body and defining a pressure sensing chamber therebetween. The pressure sensing chamber is adapted and configured to be placed in fluid communication with a patient's abdominal cavity. The second insert is arranged in the housing proximal the first insert, and has a substantially annular configuration and a plurality of apertures defined therein for allowing passage of spent insufflation fluid to pass therethrough. The third insert is arranged in the housing proximal the second insert, and has a substantially annular configuration. The housing, first, second and third inserts define respective walls of a fluid return plenum, which is adapted and configured to collect spent insufflation fluid. The fourth insert is arranged in the housing proximal the third insert, and has a substantially annular configuration and substantially tubular member extending distally therefrom. A nozzle defined between the substantially tubular member and a central portion of the third insert. The housing and third and fourth inserts define a fluid supply plenum in fluid communication with the nozzle.

The trocar can further include sound attenuation elements arranged in a proximal sound attenuation chamber arranged proximal to the fluid supply plenum. The first insert can include at least one aperture defined in the sidewall thereof to attenuate a sound created by airflow through the first insert.

In accordance with still another embodiment of the invention, a trocar for use in a minimally-invasive surgical procedure is provided. The trocar has an elongated body, a fluid return plenum, and a fluid supply plenum. The body has a lumen extending therethrough, with the proximal end portion of the body defining a housing. The fluid return plenum is defined in the housing and is adapted and configured to collect spent insufflation fluid. The fluid supply plenum is defined in the housing and arranged proximal the fluid return plenum. The fluid supply plenum is adapted and configured to deliver pressurized insufflation fluid to a nozzle in fluid communication therewith. The nozzle is configured and adapted for directing pressurized fluid into the lumen.

In accordance with this embodiment or other embodiments set forth herein, the trocar can further include a pressure sensing chamber defined in a distal end portion of the housing, distal the fluid return plenum, adapted and configured to be placed in fluid communication with a patient's abdominal cavity.

In accordance with still another embodiment of the invention, a trocar for use in a minimally-invasive surgical procedure is provided having an elongated body, a pressure sensing chamber, a safety valve and a fluid supply plenum. The elongated body has a lumen extending therethrough, and the proximal end portion of the body defines a housing. The pressure sensing chamber is defined in a distal end portion of the housing, and is adapted and configured to be placed in fluid communication with a patient's abdominal cavity. The safety valve is arranged in the housing, is in fluid communication with the pressure sensing chamber and configured and is adapted to relieve pressure from within a patient's abdominal cavity in a case of abdominal pressure exceeding a predetermined limit. The fluid supply plenum is defined in the housing, arranged proximal the fluid return plenum, and is adapted and configured to deliver pressurized insufflation fluid to a nozzle in fluid communication therewith. The nozzle is configured and adapted for directing pressurized fluid into the lumen.

If desired, a pressure relief valve in direct fluid communication to the outside of the trocar, and the surrounding environment, can also be in communication with the return plenum. Such a pressure relief valve prevents outside air from being sucked into the plenum but allows overpressure fluid to escape, harmlessly.

In accordance with the invention, a method of sealing a pressurized cavity of a patient for a surgical procedure is provided. The method includes the steps of providing a trocar for use in a minimally invasive surgical procedure, supplying a flow of pressurized fluid to the fluid supply plenum, recovering a flow of spent insufflation fluid from the fluid return plenum, recycling at least a portion of the spent insufflation fluid received from the return plenum to the fluid supply plenum, inserting a surgical instrument through the lumen of the trocar, whereby the pressurized fluid supplied to the fluid supply plenum forms a seal around the surgical instrument, thereby preventing loss of pressure within the cavity of the patient. In accordance with this method, the trocar includes an elongated body, a fluid return plenum and a fluid supply plenum. The elongated body has a lumen extending therethrough, and the proximal end portion of the body defines a housing. The fluid return plenum is defined in the housing, and is adapted and configured to collect spent insufflation fluid. The fluid supply plenum is defined in the housing, is arranged proximal the fluid return plenum, and is adapted and configured to deliver pressurized insufflation fluid to a nozzle in fluid communication therewith. The nozzle is configured and adapted for directing pressurized fluid into the lumen. The method can further include the step of filtering the insufflation gas during the step of recycling. Additionally, the step of inserting a second surgical instrument through the lumen of the trocar, whereby the pressurized fluid supplied to the trocar seals around and between the first and second surgical instruments, preventing loss of pressure within the cavity of the patient can be included.

It is noted that although the term "trocar" is used herein, the term is intended to mean a surgical access device, that allows insertion of surgical instruments, a surgeon's hand or the like, into a surgical cavity, while maintaining insufflation pressure.

It is to be understood that any feature described in connection with any particular embodiment set forth herein can advantageously be applied to other embodiments set forth herein, or indeed, to variations of embodiments not specifically set forth herein, and still be in keeping with the spirit of the present invention. It is also to be understood that both the foregoing general description and the following detailed description are exemplary and are intended to provide further explanation of the invention claimed.

BRIEF DESCRIPTION OF THE DRAWINGS

So that those having ordinary skill in the art to which the subject invention pertains will more readily understand how to make and use the devices and systems of the subject invention, preferred embodiments thereof will be described in detail hereinbelow, with reference to the drawings, wherein:

FIG. 9A is a cross-sectional view of a trocar in accordance with a further embodiment the present invention, having a proximal ball valve and a proximally arranged fluid collection chamber;

FIG. 9B is an enlarged partial cross-sectional view of the trocar of FIG. 9A, illustrating detail in the proximal end portion thereof;

FIG. 11 is a cross-sectional view of a trocar in accordance with a further embodiment the present invention, having a safety valve incorporated therewith and a removable proximal cap;

FIG. 12 is an enlarged partial cross-sectional view of the trocar of FIG. 11, illustrating detail in the proximal end portion thereof;

FIG. 16 is an alternate embodiment of the system of FIGS. 14 and 15, wherein main components of the system are housed in a single unit;

FIG. 17 is an isometric view of a second embodiment of an insufflation and circulation system in accordance with the invention;

FIG. 18 is an example schematic representation of the main components included within the system of FIG. 17;

DETAILED DESCRIPTION OF THE PREFERRED EMBODIMENT

The devices, systems and methods presented herein may be used for creating and maintaining a surgical pathway through the abdominal wall of a patient undergoing minimally invasive surgery. The present invention is particularly suited for minimally invasive surgeries performed under insufflation, such as laparoscopic removal of a gall bladder.

Figure 1:
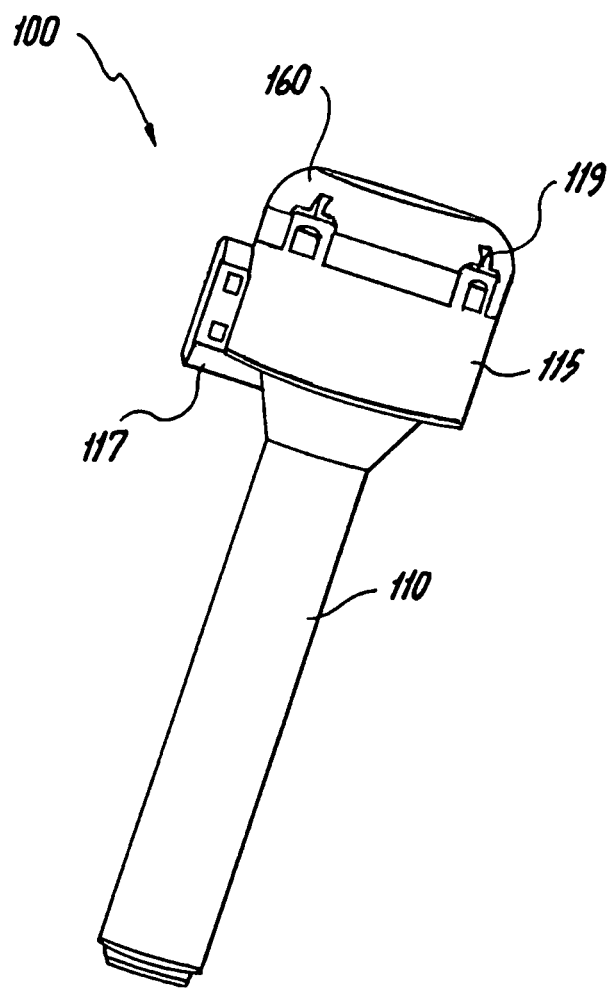
FIG. 1 is an isometric view of a trocar in accordance with one embodiment of the present invention.
Figure 2:
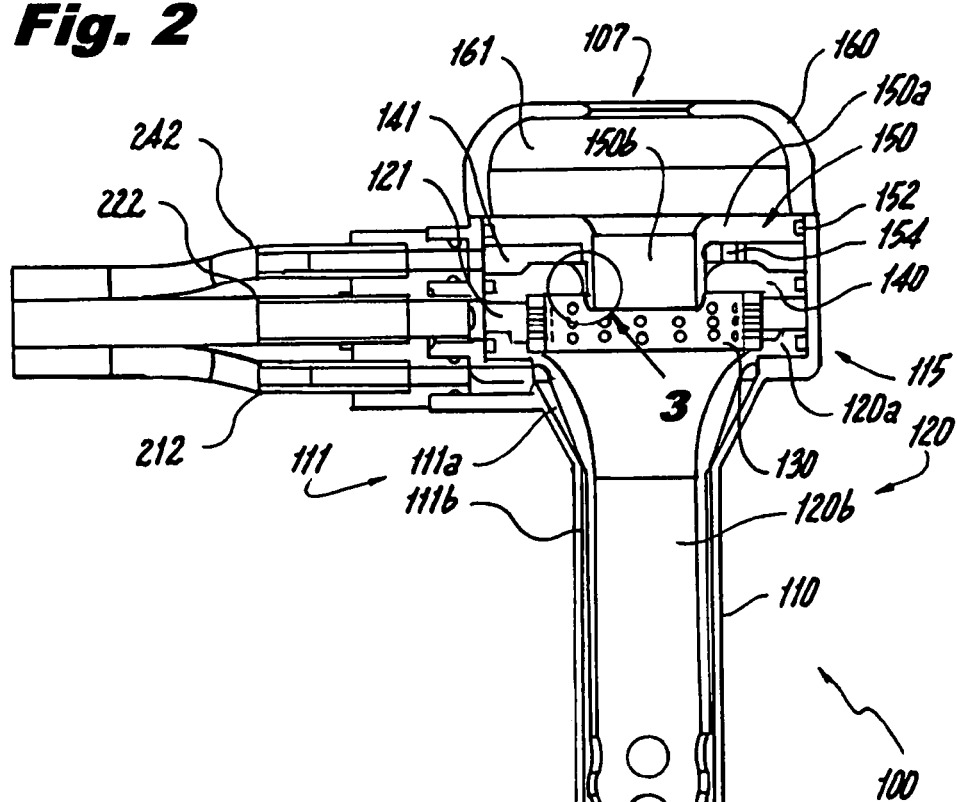
FIG. 2 is a cross-sectional view of the trocar of FIG. 1.
Figure 3:
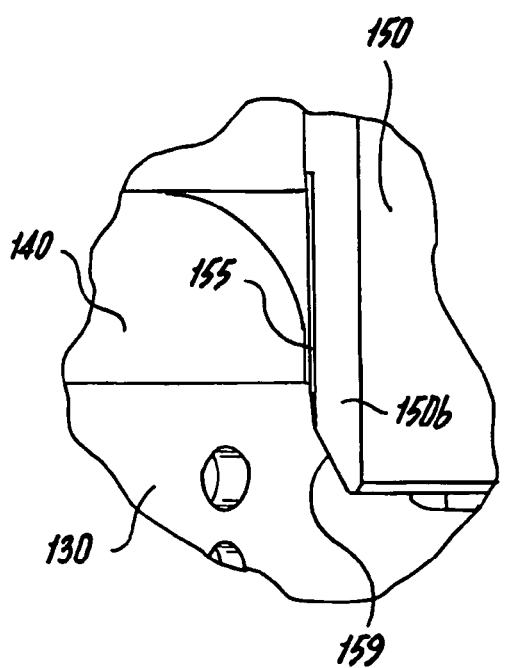
FIG. 3 is an enlarged view of the respective portion of FIG. 2, illustrating the nozzle in detail.

For the purposes of explanation and illustration, and not limitation, referring now to the drawings, wherein like reference numerals identify similar structural aspects of the subject trocars and systems therefor, a first exemplary embodiment of a trocar in accordance with the invention is shown in FIGS. 1-3, and is designated generally by reference character 100. Other embodiments of trocars in accordance with the invention, related systems or aspects thereof, are provided in subsequent figures, which are described in detail below.

FIG. 1 is a side view, and FIG. 2 is cross-sectional view of a trocar 100 constructed in accordance with the invention. The trocar includes a central lumen 107, which is defined by various elements, and which extends longitudinally, through the center of the trocar 100. The trocar 100 includes a body 110, including a housing 115 defined in the proximal end portion thereof. A connection block 117 extends from the housing 115 and facilitates connection between the trocar 100 and fluid conduits connected thereto, as best shown in FIG. 2.

Defined within the housing 115 are a pressure sensing chamber 111 including a pressure sensing plenum 111a, which is in fluid communication with a pressure sensing channel 111b. The pressure sensing chamber 111 is defined between the body 110 and a body insert 120, including a substantially tubular portion 120b and a substantially annular portion 120a. This arrangement of the pressure sensing chamber allows the remainder of the system, described hereinbelow, to be in fluid communication with the abdominal cavity, so that the abdominal pressure can be monitored and controlled. As shown in FIG. 2, a pressure sensing conduit 212 is in fluid communication with the pressure sensing chamber 111, which in-turn connects with a control unit of the system, described in more detail hereinbelow. Further, apertures 125 can be formed in the wall of the tubular portion 120b of the body insert 120. These apertures 125 can be arranged so as to alter the acoustic properties of the tubular portion 120b, by reducing the effective length of the tubular portion 120b. Accordingly, the wavelength of sound produced by fluid passing through the lumen 107 can be adjusted so that it is more easily canceled out by other sound attenuation elements, such as those housed within the cap 160.

The annular portion 120a of the body insert 120 separates the pressure sensing chamber 111 and a fluid return plenum 121. The fluid return plenum is further defined by the housing 115 on its outer periphery, a second diffuser insert 130 on its inner periphery, and an annular insert 140 having a substantially annular configuration. The second diffuser insert 130 serves in-part, to maintain spacing between the body insert 120 and the annular insert 140. The fluid return plenum 121 allows for collection of spent insufflation fluid—fluid moving proximally, returning from within the lumen of the tubular portion 120b of the body insert 120. Apertures defined in the second insert promote even evacuation of fluid from about the circumference of the lumen 107 in the region of the fluid return plenum 121. Fluid is removed from the fluid return plenum 121 through a fluid return conduit 222 and can be recirculated, such as through the systems embodied in FIGS. 14-18.

The fourth insert 150 includes a substantially annular portion 150a and a substantially tubular portion 150b. One or more standoffs 154 can be provided on the fourth insert 15, or alternatively the annular insert 140, to maintain spacing of the fluid supply plenum 141 defined therebetween. Additionally, a nozzle 155 is defined between the annular insert 140 and a fourth insert 150. The precise geometry of the annular insert 140 and fourth insert 150, and the spacing therebetween allow for a continuous stream of fluid which serves to effectively seal the lumen 107, and inhibit escape of insufflation fluid. The lower outer circumferential edge 159 of the tubular portion 150b of the fourth insert 150 is angled inward, which directs the continuous stream of fluid centrally. The fluid follows the contour of this surface 159, and is thus directed centrally, at least in part due to the Coanda effect. Fluid is supplied to the fluid supply plenum 141 through a fluid supply conduit 242. Preferably, the fluid return conduit 222 is larger in diameter than the fluid supply conduit 242, as returning fluid is depressurized and therefore occupies an increased volume. To maintain equivalent mass flow rates for supplied and returned fluid, the diameter of the fluid return conduit 222 should have a larger diameter. pressurized insufflation fluid can be supplied to the trocar 1000 through systems such as those embodied in FIGS. 14-18.

Additionally, any of the inserts can be sealed to the housing 115 to create fluid-tight seals therebetween. In the illustrated embodiment, grooves 152 are provided between the body insert 120, annular insert 140 and fourth insert 150 and the housing 115, respectively. In these grooves, a sealing element, such as an O-ring can be placed.

A cap 160 is provided at the proximal end of the trocar 100. As illustrated in FIG. 1, the cap 160 can be affixed to the housing 115 by way of a snap fit arrangement. In this case, protrusions on the cap 160 each engage a pawl 119 on the housing 115. Naturally, any other suitable connection can be used, including but not limited to friction fit, a latch, adhesive, solvent welding, ultrasonic welding, heat welding and mechanical fasteners such as a hook- and loop fastener. Accordingly, the cap 160 can be permanently installed or can be removable from the remainder of the trocar 100. Further, as illustrated, the cap 160 can extend past the joint between the fourth insert 150 and the housing 115, effectively preventing proximal movement of any insert held within the housing 115.

The cavity 161 defined by the cap 160, with the exclusion of the volume necessary in the lumen 107 for passage of surgical implements, can include sound absorbing material and/or baffles to reduce noise emitted from the trocar 100. In combination with the apertures 125 formed in the body insert 120, sound emitted can be reduced significantly by mutually tuning these sound attenuating features.

Figure 5:
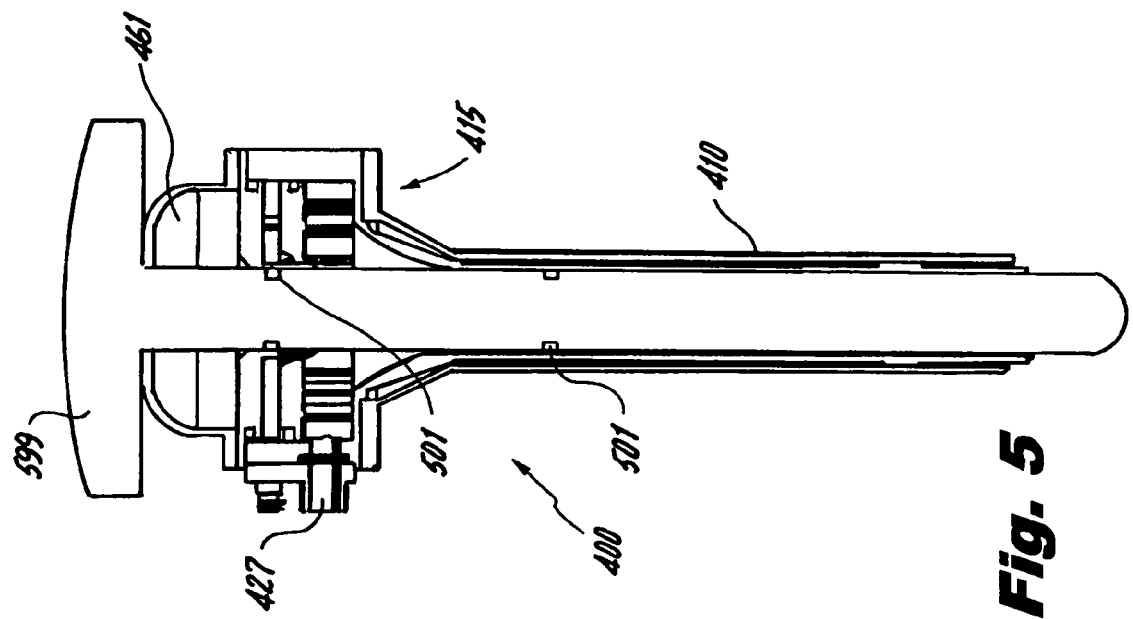
FIG. 5 is a cross-sectional view of the trocar of FIG. 4 with an obturator inserted therethrough.
Figure 4:
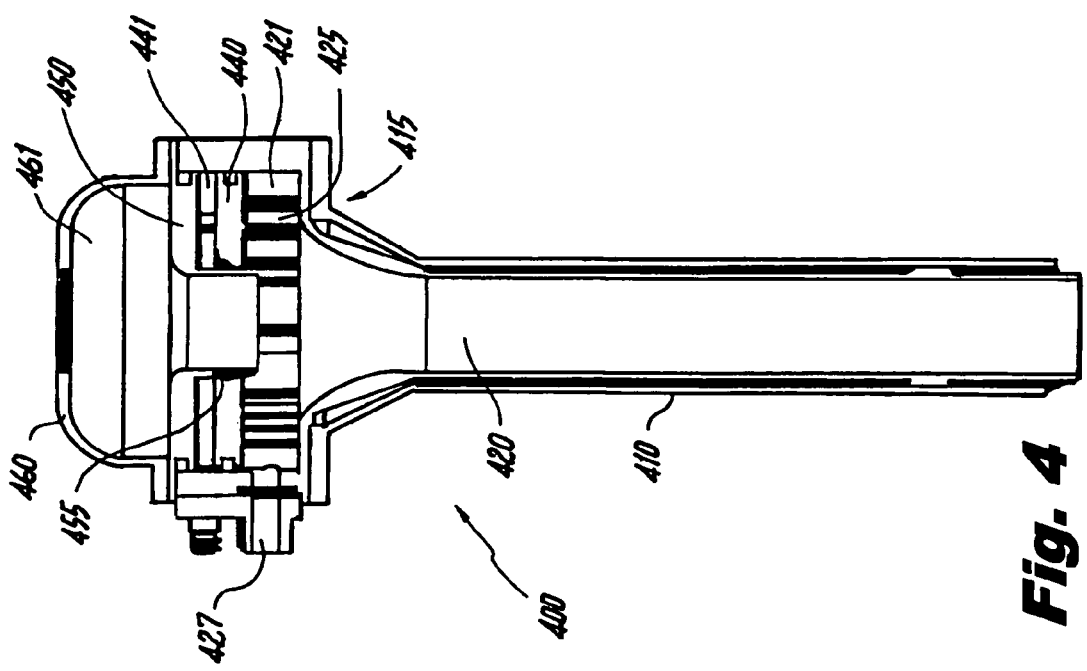
FIG. 4 is a cross-sectional view of a trocar in accordance with a further embodiment the present invention.

FIGS. 4 and 5 illustrate a second embodiment of a trocar 400 constructed in accordance with the invention, with FIG. 5 illustrating the trocar 400 having an obturator 599 inserted therein. Distinguishing of this embodiment, as compared with the embodiment of FIGS. 1-3, is the fluid return plenum 421. Instead of providing an annular insert having a plurality of apertures formed therein, a plurality of baffles 425 are provided, which act as a standoff to maintain spacing within the housing 415 of the trocar 400, and can be adapted to enhance noise reduction by absorbing sound. Additionally, sound absorbing material can be laced in the fluid return plenum 421 to further enhance noise reduction.

As with the embodiment of FIGS. 1-3, the embodiment of FIGS. 4 and 5 includes a body insert 420 inserted into the body 410. The baffles 425 are integrally formed with an insert, such as the body insert 420 or annular insert 440, but alternatively can be formed independently and separately inserted in the housing 415. The annular insert 440, in conjunction with a nozzle insert 450, together define the nozzle 455 and define the fluid supply plenum 441. Similarly, the fluid return plenum 421 is defined on the distal side of the annular insert 440, and is in fluid communication with a fluid return port 427. Further, a cap 460 can be provided at the proximal end portion of the trocar 400, and can include sound attenuation materials therein.

As shown in FIG. 5, the obturator 599 has been designed for the recirculation system and devices disclosed herein. The obturator has O-rings 501 proximal and distal to the jets that fit tightly into the cannula. With the obturator 599 installed the O-rings 501 maintain a seal against gas escaping from the abdomen through the trocar 400. The O-rings 501 also contain the jet flow within the trocar 400. The supply can be pumped to the trocar prior to insertion. The gas will pass through the jets and out the return line without creating any blowing effects external to the trocar. Once the trocar 400 is inserted into the patient, the obturator 599 can be removed and the air seal will be established without losing pneumoperitoneum.

Figure 7:
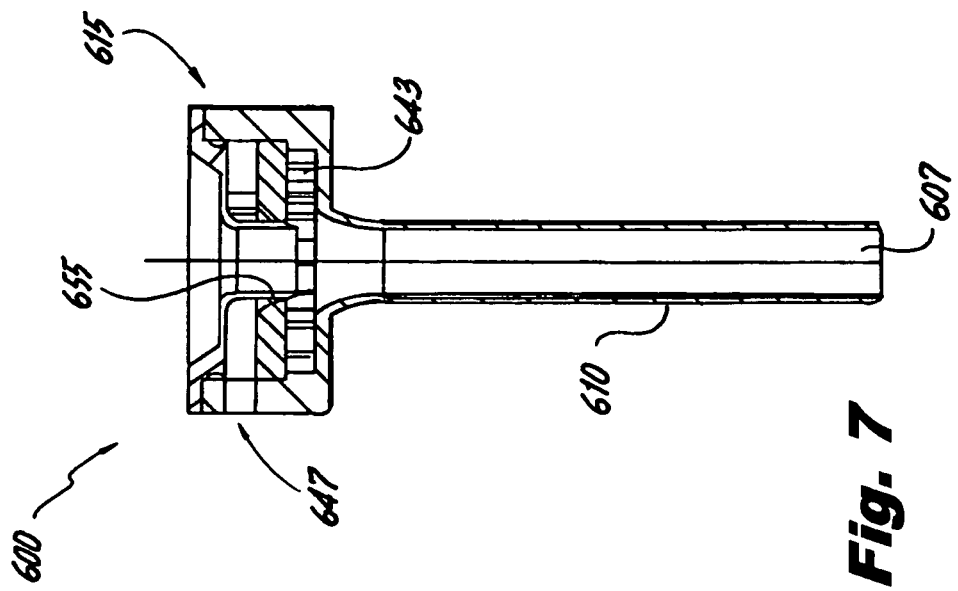
FIG. 7 is a cross-sectional view of the trocar of FIG. 6, rotated about its longitudinal axis.
Figure 6:
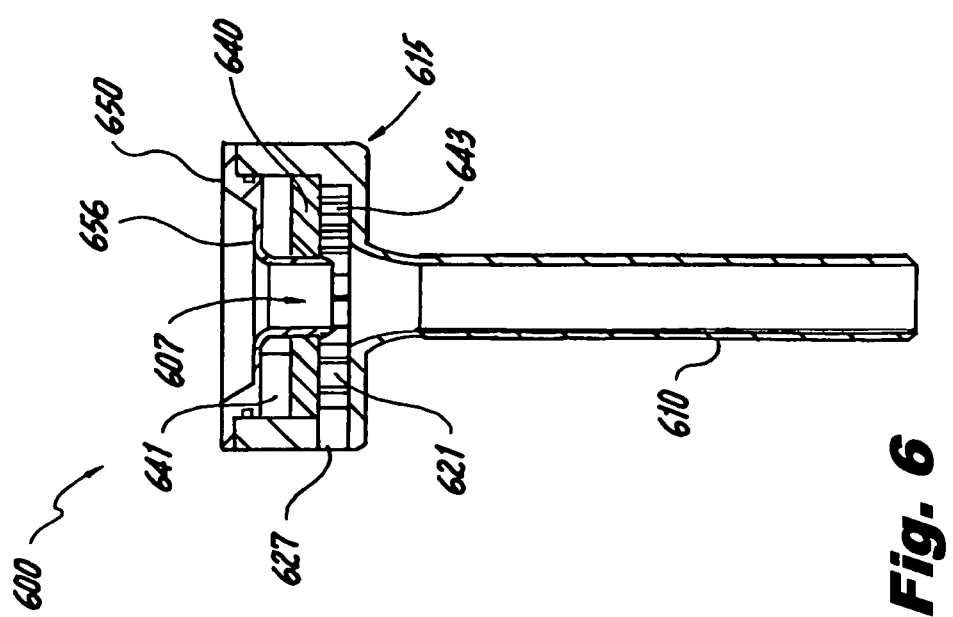
FIG. 6 is a cross-sectional view of a trocar in accordance with still a further embodiment the present invention.

FIGS. 6 and 7 illustrate a third representative embodiment of a trocar 600 in accordance with the invention. The trocar 600 is similar to the foregoing embodiments, but does not include either a pressure sense plenum, or a proximal cap. The trocar 600 includes a body 610, having a housing 615 arranged at the proximal end portion thereof. Baffles 643, an annular insert 640 and nozzle insert 650, respectively define, in conjunction with the housing 615, a fluid return plenum 621, a fluid supply plenum 641, a central lumen 607 and a nozzle 655. The nozzle insert 650 is formed so as to have a depressed region 656 which helps guide surgical instruments to the lumen 607. A return fluid port 627 (FIG. 6) is formed through the housing 615 and is in fluid communication with the fluid return plenum. A fluid supply port 647 (FIG. 7) is similarly formed through the housing 615 and is in fluid communication with the fluid supply plenum 641.

Figure 8A:
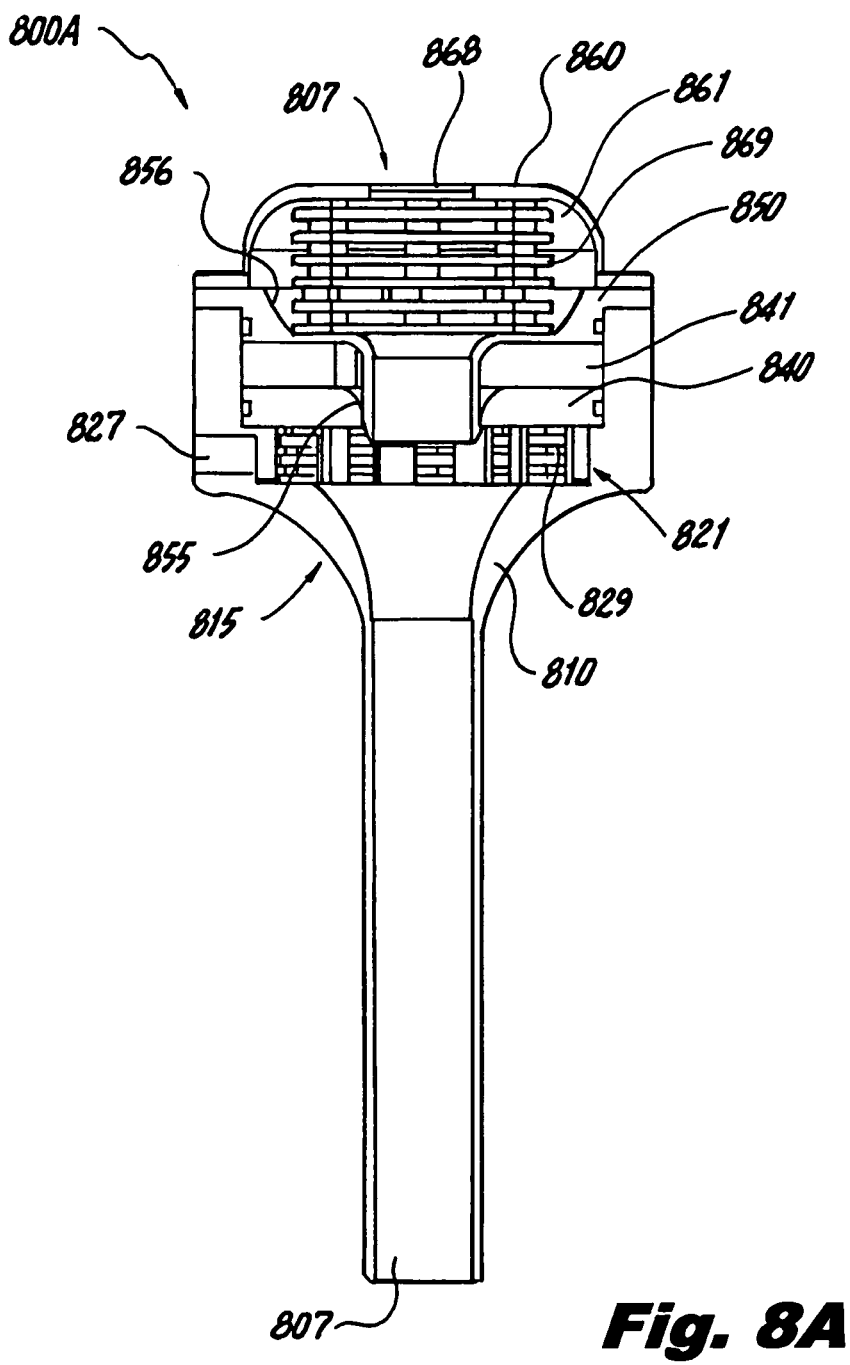
FIG. 8A is a cross-sectional view of a trocar in accordance with still another embodiment the present invention having proximal and distal sound attenuation chambers in the housing thereof.

FIG. 8A illustrates yet another trocar 800A constructed in accordance with the present invention. The trocar 800A includes a body 810, having a housing 815 arranged at the proximal end portion thereof. Distal baffles 829, an annular insert 840 and nozzle insert 850, respectively define, in conjunction with the housing 815, a fluid return plenum 821, a fluid supply plenum 841, a central lumen 807 and a nozzle 855. The nozzle insert 850 is formed so as to have a depressed region 856 which helps accommodate proximal baffles 869 within the chamber 861 defined by a proximal cap 860. A reduced aperture 868 can be provided at the proximal end portion of the cap 860. Optionally, an annular seal can be provided therein in order to further seal the lumen 807 against a surgical instrument when the surgical instrument is inserted therethrough.

A return fluid port 827 is formed through the housing 815 and is in fluid communication with the fluid return plenum 821. A fluid supply port is similarly formed through the housing 815 and is in fluid communication with the fluid supply plenum 841. As with the foregoing embodiment, no pressure sense chamber is provided, but as is the case with the foregoing embodiment or any embodiment set forth herein, such pressure sense capability can be imparted by providing such a chamber in another, similar trocar or as a separately inserted needle into the abdomen of the patient.

Figure 8B:
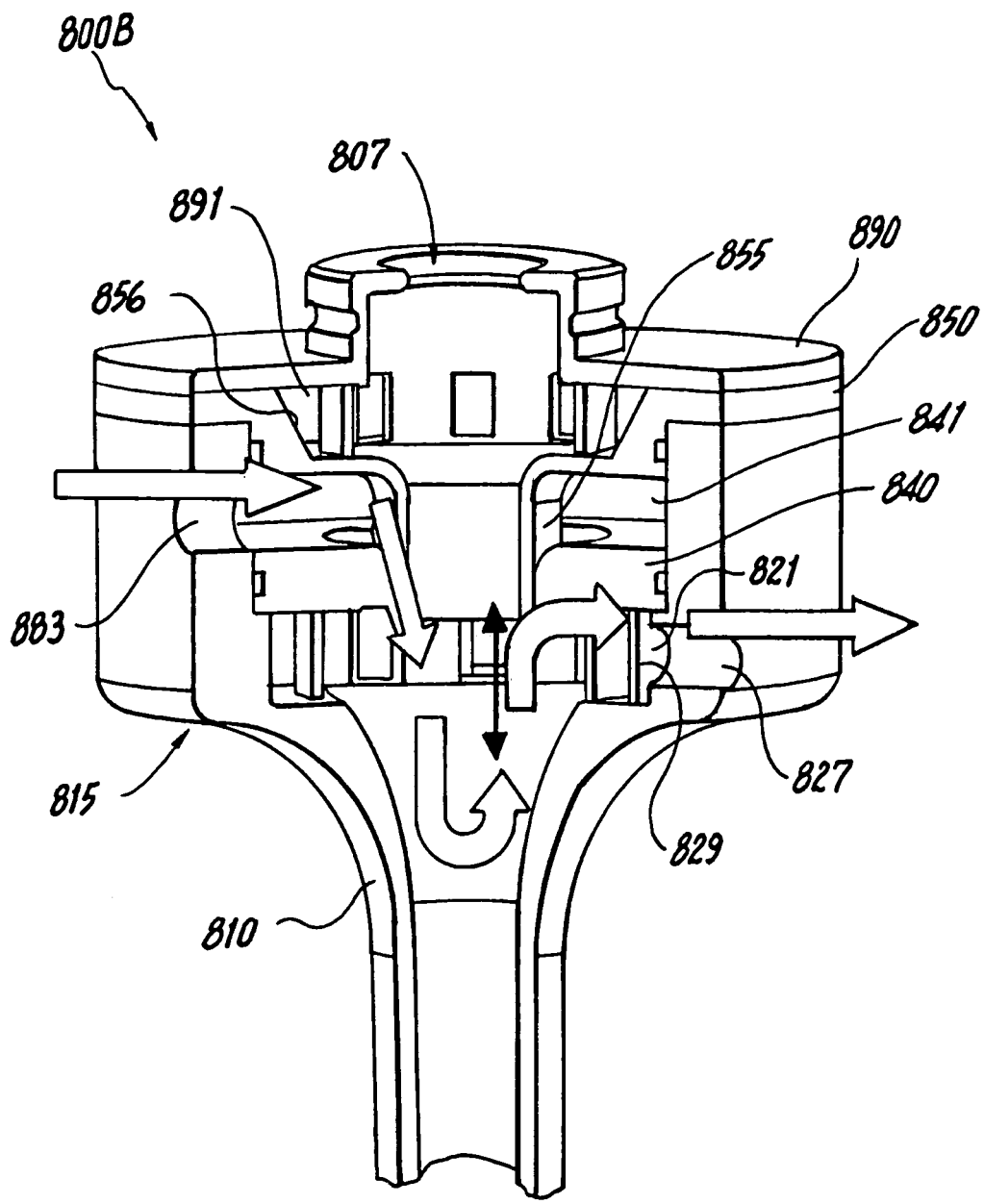
FIG. 8B is a cross-sectional view of a trocar in accordance with still another embodiment the present invention having proximal and distal sound attenuation chambers in the housing thereof, and a proximal adapter portion for engaging a removable cap.

FIG. 8B illustrates a trocar 800B having an alternate arrangement of the proximal end thereof, but otherwise similar to trocar 800A of FIG. 8A. The trocar 800B includes a body 810, having a housing 815 arranged at the proximal end portion thereof. Distal baffles 829, an annular insert 840 and nozzle insert 850, respectively define, in conjunction with the housing 815, a fluid return plenum 821, a fluid supply plenum 841, a central lumen 807 and a nozzle 855. The nozzle insert 850 is formed so as to have a depressed region 856 which helps accommodate a proximal sound attenuation chamber 891, in cooperation with a proximal cap adapter insert 890. Sound absorbing material can be provided in the sound attenuation chamber 891 to help reduce noise emitted by the flowing fluid within the trocar 800B. The cap adapter insert 890 can facilitate engagement between the trocar 800B and a cap, such as one containing a ball valve, for example.

A return fluid port 827 is formed through the housing 815 and is in fluid communication with the fluid return plenum 821. A fluid supply port 883 is similarly formed through the housing 815 and is in fluid communication with the fluid supply plenum 841.

In each of the foregoing embodiments, fluid return plena have been arranged distally, with respect to the fluid supply plena in each trocar embodiment. However, alternatively, the fluid return plenum may be arranged proximally, with respect to the fluid supply plenum. Such an arrangement is illustrated in connection with the trocar 900 illustrated in FIGS. 9A and 9B.

The trocar 900 of FIGS. 9A and 9B includes a body 910, an annular insert 940 and a nozzle insert 950. A nozzle 955 is defined between the annular insert 940 and the nozzle insert 950. A fluid supply plenum 941 is defined in the housing 915 between the annular insert 940 and nozzle insert 950 and is fed by fluid supply port 947. The fluid return plenum 921 is defined proximal the nozzle insert 950, by the nozzle insert 950 and an optional secondary seal element 980, secured to the housing. The secondary seal element 980 is secured to the housing and includes an annular seal 983 to facilitate sealing against instruments inserted through the lumen 907 of the trocar 900. If a complete seal is made between an instrument and the seal element, no fluid can escape through the proximal end of the lumen. Accordingly, if desired, the system that provides insufflation fluid for the purpose of creating a fluid seal in the trocar 900, can be switched off for the duration during which a seal is maintained with the sealing element 980.

Baffles 991 and/or sound absorbent material can be arranged in the fluid return plenum 921 to reduce noise emitted from the trocar 900 when in use. Fluid is exhausted from the fluid return plenum 921 through return fluid port 993. The proximal cap 960 may be permanently or temporarily affixed to the remainder of the trocar 900, and includes a magnetic ball valve, having a ball 967, which engages a ring 968 formed in the cap 960. As embodied, either the ball 967 or the ring 968 can be magnetic, with the other being ferrous. Alternatively, the ring 968 can be embodied as an electromagnet, having power supplied thereto, with the ball 967 being ferrous and therefore attracted to the ring 968 electromagnetic ring when switched on.

Figure 10:
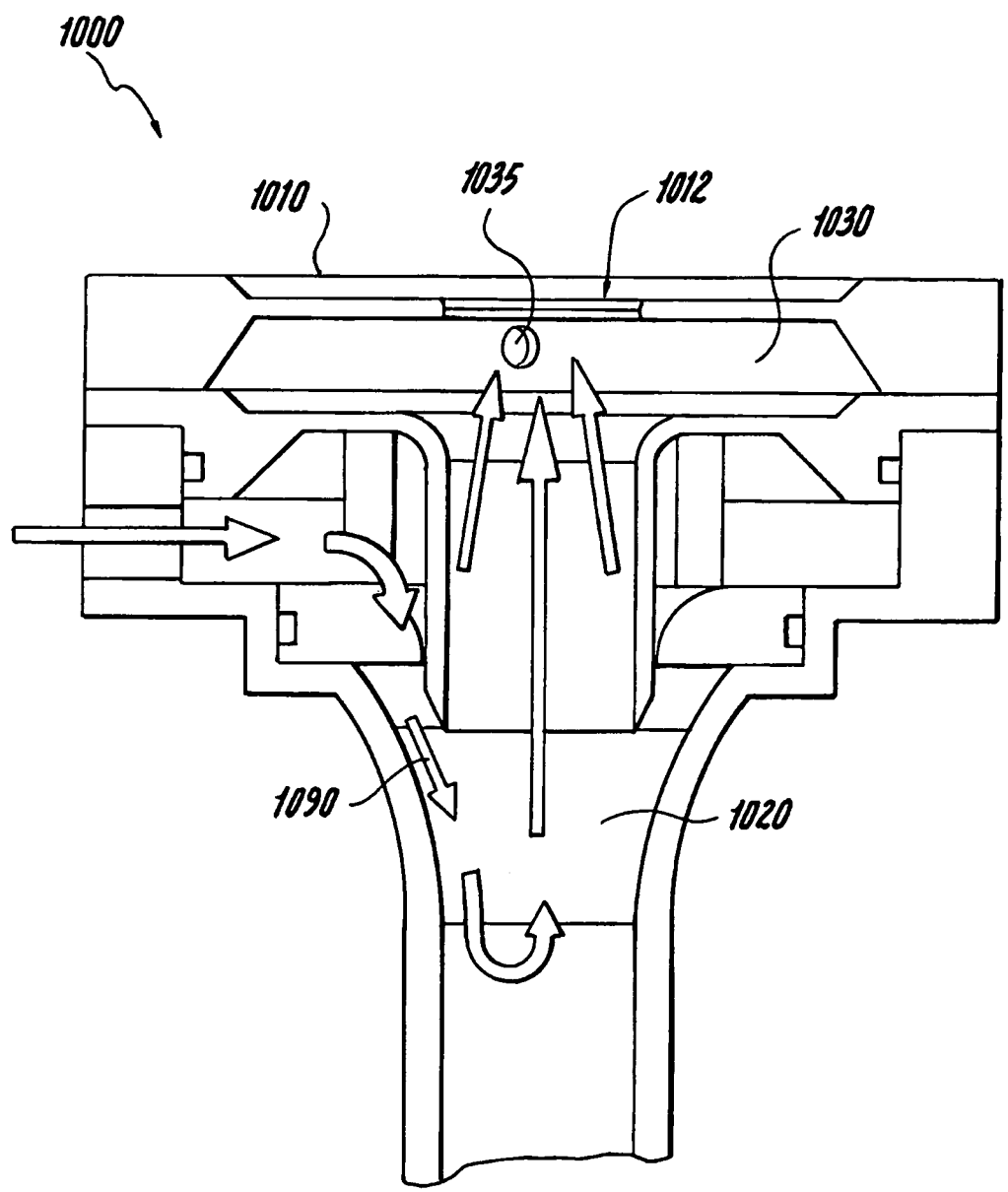
FIG. 10 is a cross-sectional view of a further trocar in accordance with the present invention, having a proximal fluid collection chamber.

Referring to FIG. 10, which illustrates a further embodiment of a trocar 1000 in accordance with the invention, while forming a fluidic seal, the distal motion of the gas is slowed and reversed to an outward flow as it is acted on by pressure within the abdomen. The gas, spent of inward momentum, is pushed proximally, normally through the lumen of the surgical access device. As the spent gas exits the proximal end of the lumen 1020 of the surgical access device 1000, the gas, represented by arrows 1090, will enter a collection chamber 1030 which may also serve to house sound abatement material. The chamber 1030 will be connected to a return line via a port 1035 formed therein, through which a recirculation pump (e.g., pump 1940 of FIG. 19) will extract the exiting gas. During use, supplemental gas (e.g., carbon dioxide) can be added to the system as needed, to insure that the net flow of gas through the proximal end 1010 of the access device 1000 is in the proximal direction. This will ensure that the return flow to the recirculation pump is the desired gas (e.g., carbon dioxide) rather than air drawn into the access device 1000 through the proximal opening 1012. Depending on the precise implementation, a mechanical valve can be provided at the proximal end of the surgical access device. Such a valve can act to further eliminate the potential of drawing external air into the system from the outside.

FIGS. 11 and 12 are partial proximal end cross-sectional views of a further embodiment of a trocar 1100 constructed in accordance with the invention. The trocar 1100 includes a body 1110 having a proximal housing 1115. The nozzle 1155 is formed between the housing 1110 and a nozzle insert 1150, between which is also defined a fluid supply plenum 1141. A safety valve 1180 formed in the housing 1115. In this embodiment, a pressure sensing channel and plenum 1111 are formed between the body 1110 and a tubular member 1120 placed over the body 1110.

The safety valve 1180 is configured so as to be urged closed by way of a spring (not shown), but alternate methods of maintaining the valve 1180 closed by maintaining the ball 1181 in contact with a seat are possible. The safety valve 1180 is in fluid communication with the pressure sensing plenum 1111 by way of a fluid conduit 1184. When pressure within the abdominal cavity exceeds a predetermined safe limit, the ball 1181 is urged away from its seat, the spring compressed, and thus the channel 1184 is uncovered. pressurized fluid then exits exhaust conduits 1185a, 1185b and 1185c. When the pressure in the abdomen subsequently drops, the valve 1180 closes.

The trocar 1100 of FIGS. 11 and 12 includes a cap 1170 removably secured thereto. The cap includes a chamber 1161 defined therein for use with sound attenuation features such as baffles and/or sound absorbing material.

Figure 13:
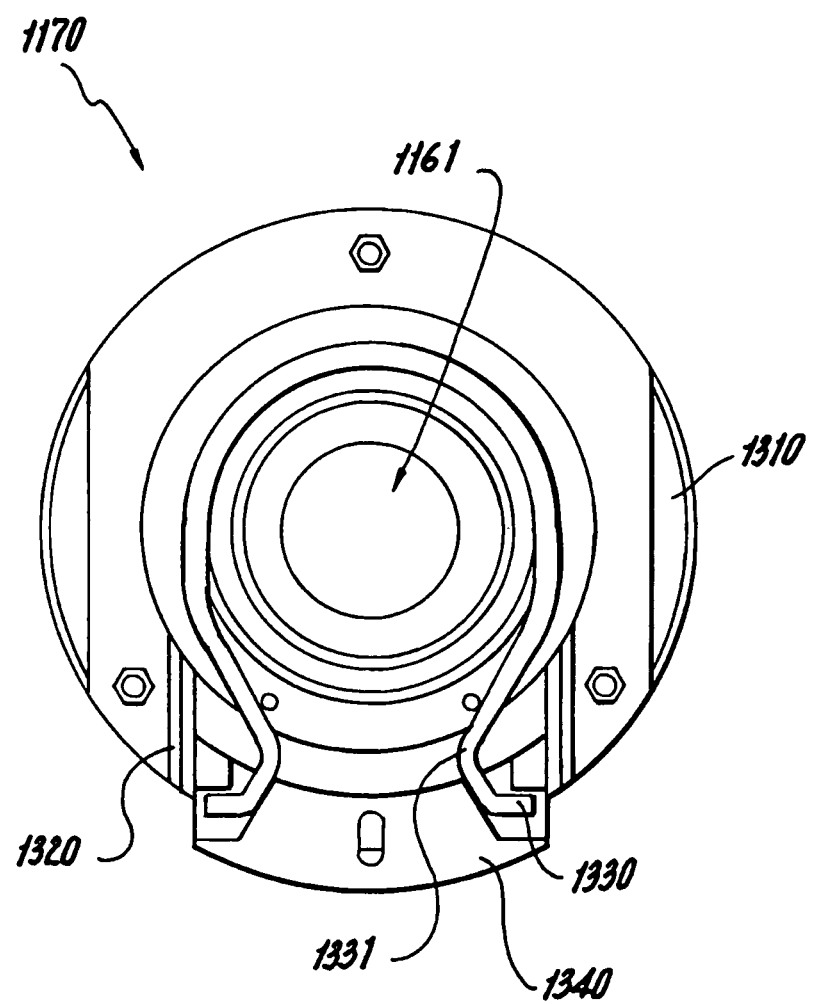
FIG. 13 is a cross-sectional view of the cap of the embodiment of FIGS. 11 and 12.

As shown in FIG. 13, which is a lateral cross-sectional view of the cap 1170 of FIGS. 11 and 12, the body 1310 includes a track 1320, which engages a mating track on the trocar 1100. A resilient locking member 1330 engages a matching groove in the trocar 1100. Depressing the button 1340 causes the locking member 1330 to deflect and open at its neck 1331. This allows insertion onto and removal from the trocar 1100.

In further accordance with the invention, various systems for surgical insufflation and/or for use in creating and maintaining fluid seals in cannulas constructed in accordance with the invention are provided. FIGS. 14-18 illustrate such systems.

Figure 14:
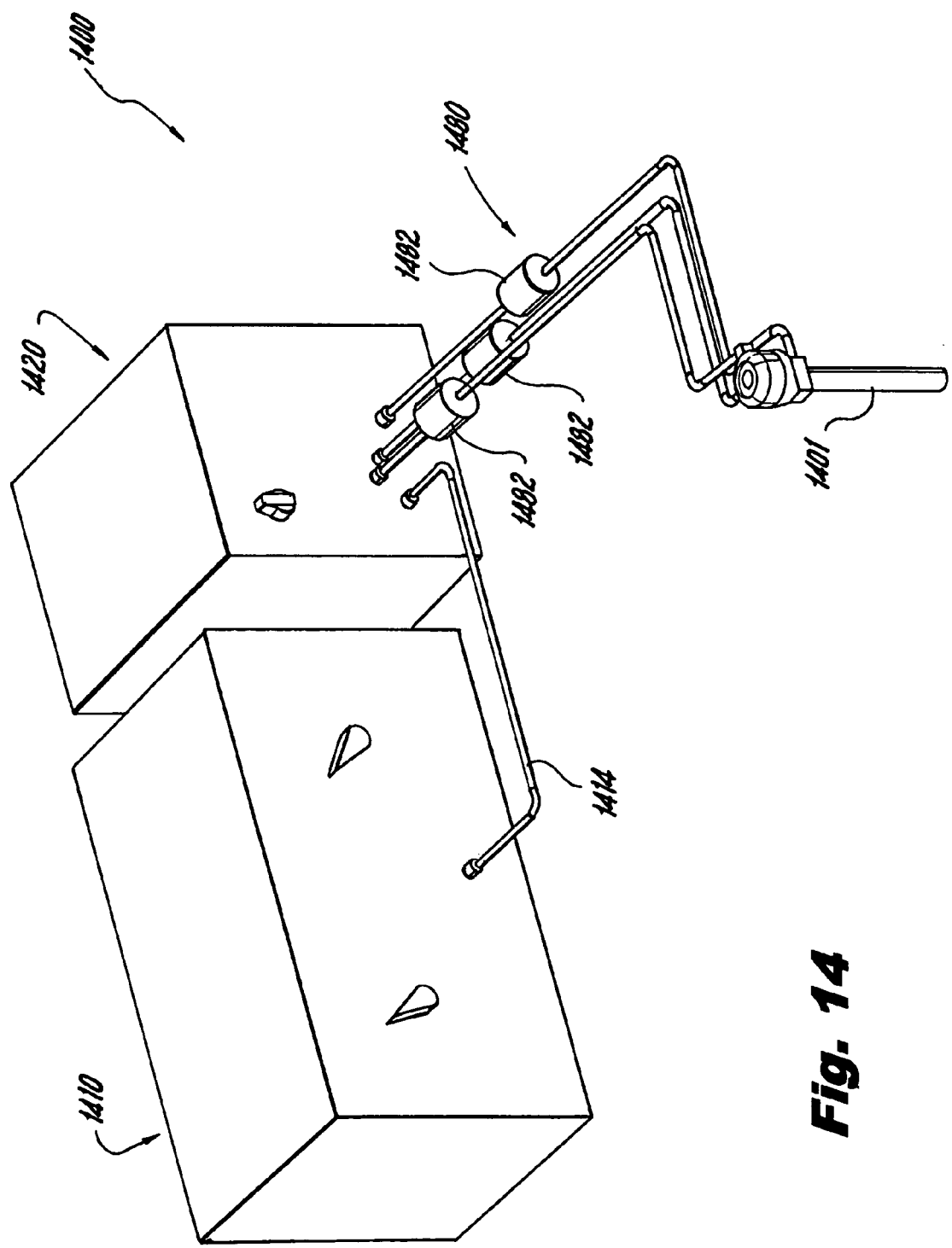
FIG. 14 is an isometric view of one embodiment of an insufflation and circulation system in accordance with the invention.
Figure 15A:
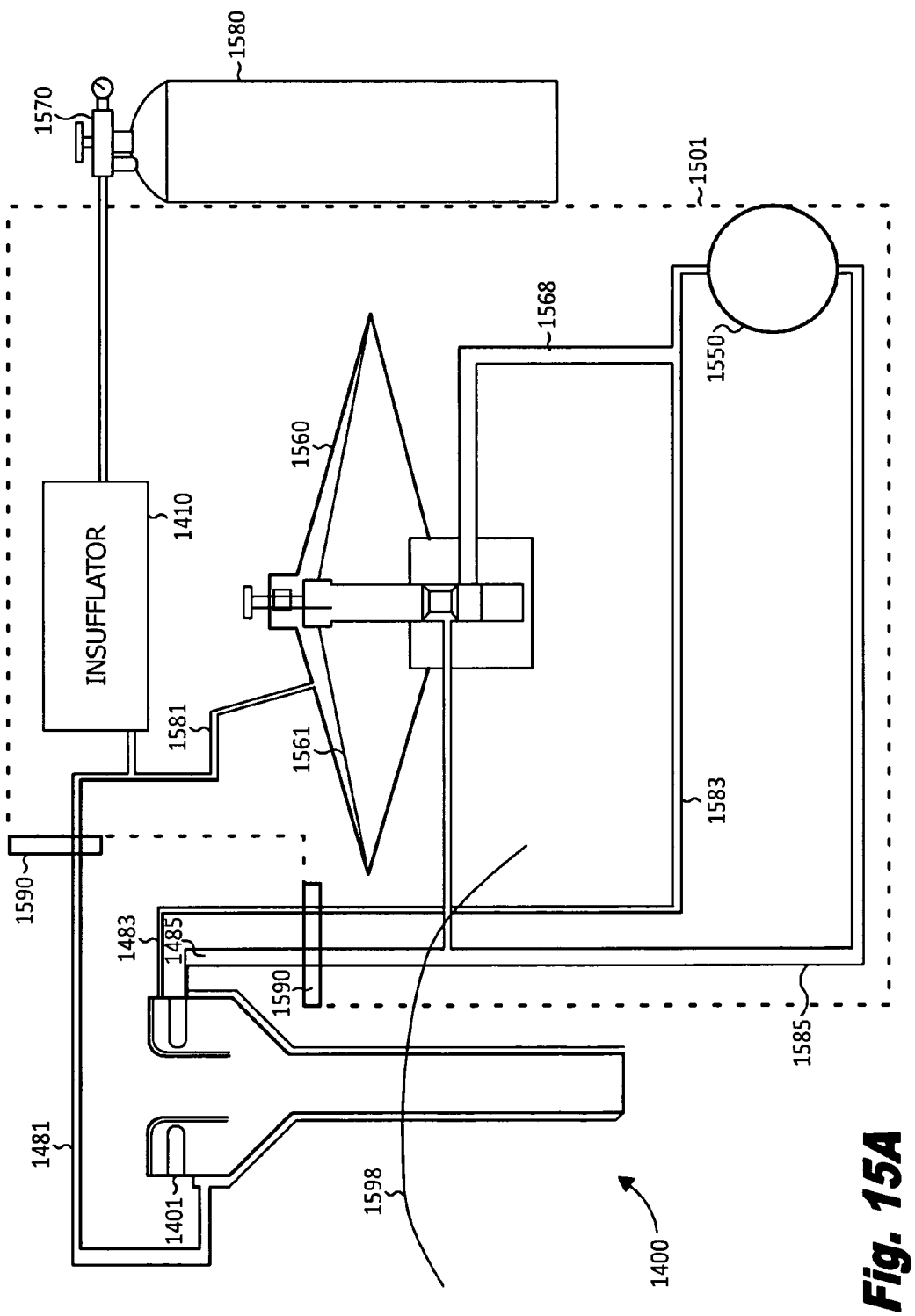
FIG. 15A is an example schematic representation of the main components included within the system of FIG. 14.

In the embodiment of FIGS. 14 and 15A, which illustrate a system for surgical insufflation and sealing, a control unit 1420 is shown in connection with a surgical insufflator 1410 and a surgical trocar 1401, in accordance with one system embodiment of the invention. The trocar 1401 is connected to the control unit 1420 by way of fluid conduits 1480, and the insufflator is connected with the control unit 1410 by way of another fluid conduit 1414. As shown in FIG. 15A, the insufflator 1410 receives insufflation fluid from a source, in this case, a tank 1580. A pressure regulator 1570 is provided between the tank 1580 and the insufflator 1410.

The insufflator output is in fluid communication with a pressure sensing line 1481 leading to the trocar 1401, and with a pressure sensing line 1581 leading to a pressure-controlled valve 1560, housed within the control unit 1420. The control unit 1420 also includes a fluid pump 1550 for recirculating insufflation gas for the purpose of maintaining a fluid seal within the trocar 1401, and thus maintain the pneumoperitoneum within the abdomen 1598 of the patient.

The fluid is received from the trocar 1401 through return fluid conduits 1485, 1585, is pressurized by the fluid pump 1550, and is directed through the fluid supply conduits 1583, 1483 to the fluid supply plenum and nozzle of the trocar 1401. If pressure within the abdomen 1598 exceeds a predetermined safe limit, such increased pressure is communicated by way of the pressure sensing conduits 1481, 1581 to the pressure-controlled valve 1560. The pressure-controlled valve 1560 then responds by opening and short circuiting the fluid supply conduit 1583, through bypass conduit 1568, to the fluid return conduit 1585. Thus, fluid that was to be delivered to the trocar 1401 to maintain a fluid seal is reduced, and partially or fully recirculated back to the pump 1550. Accordingly, excess fluid already within the abdomen 1598 will escape until abdominal pressure decreases to an acceptable level, when the valve 1560 closes and fluid flow through the fluid supply conduits 1483, 1583 increases.

In the illustrated embodiment, a diaphragm-type valve, having an internal diaphragm 1561, is shown, but it is to be understood that alternate arrangements of pressure control are applicable to the present invention. For example, a pressure transducer can be arranged in fluid communication with the pneumoperitoneum, by placing the pressure transducer on or in the trocar 1401, or in the control unit 1420, and can be adapted and configured to control an electrically operated valve, for example.

Although illustrated as separate but connected units in FIG. 14, the insufflator 1410 and the control unit 1420 can be contained in a single housing, as indicated by dashed line 1501 in the schematic of FIG. 15A, and as illustrated by element 1620 in FIG. 16. Connectors 1590 allow connections between the control unit 1420 and fluid conduits 1481, 1483, 1485, which in-turn connect to the surgical trocar 1401. Filters are provided in line with the fluid conduits 1480, and can be housed independently as with filters 1482 of FIG. 14, or in a single housing 1682 of FIG. 16.

Insufflation gas is provided to the system 1400 from a supply, such as a tank 1580. The system 1400, which can include elements such as an insufflator 1410, pressure regulator 1570, conditioning elements, such a humidifier, dehumidifier or heater, recirculation pumps and/or other elements, receive the insufflation gas. The system 1400 can further include a safety dump valve in connection with one or more of the fluid conduits to exhaust excess insufflation fluid, if necessary.

Typical surgical insufflators operate by intermittently measuring pressure between periods of insufflation through a single fluid conduit. As embodied in FIGS. 14 and 15, the insufflator 1410 is capable of functioning normally in this regard. The insufflator 1410 can initiate insufflation of the abdomen 1598 through the pressure sensing conduit 1481, and also intermittently measure pressure therethrough. However, normal insufflator operation does not adversely affect the functioning of the pressure-controlled valve 1560. Although slight pressure surges may be caused by the insufflator, a fluid seal in the trocar is maintained.

Accordingly, in operation, when low abdominal pressure is sensed, the insufflator is triggered to insufflate the abdomen 1598, and the pressure-controlled valve 1560 remains in a closed state, with the fluid pump 1550 receiving fluid from a return fluid plenum in the trocar 1401, through the return fluid conduits 1485, 1585, and delivering pressurized fluid through the fluid supply conduits 1583, 1483 to the nozzle of the trocar 1401.

When excessive abdominal pressure is experienced, the insufflator does not provide additional insufflation fluid to the abdomen 1598, and the pressure-controlled valve 1560 opens, connecting the fluid supply conduit 1583 and the return fluid conduit 1585 through the bypass conduit 1568, thereby reducing the effectiveness of a fluid seal formed in the trocar 1401, and allowing a portion of the insufflation fluid to escape, and lowering the pressure within the abdominal cavity.

It may be desired to use a removable proximal end cap on the trocar 1401, for use during insufflation to allow the insufflator 1410 to fill the abdomen, after which time, the pump 1550 of the control unit 1420 can be actuated, and the cap removed. Alternatively, an obturator can be inserted through the trocar 1401 and mutually sealed therewith, such as by O-rings or the like.

The system 1400 pressurizes the insufflation fluid to the desired pressure and can be adapted and configured to treat or condition the fluid as necessary. As set forth above, the pressure supplied to trocars in accordance with the invention can be between about 0 mmHg and 3500 mmHg at any 0.1 mmHg increment of pressure therebetween. Such pressures are suitable for fluid supply plena, such as plenum 141 shown in FIG. 2. However, relatively high pressures can also be supplied to the nozzles of trocars in accordance with the invention, such as nozzle 155, best seen in FIG. 3. In one embodiment, pressure supplied to the nozzle(s) is between about 1000 mmHg and about 2000 mmHg, and can be at any 0.1 mmHg increment of pressure therebetween. In one preferred embodiment, the pressure supplied to the nozzle(s) is about 1530 mmHg. Naturally, normal pressures can vary as needed or desired. Moreover, pressures will decrease from normal when an excessive abdominal pressure is measured, as set forth above.

Figure 15B:
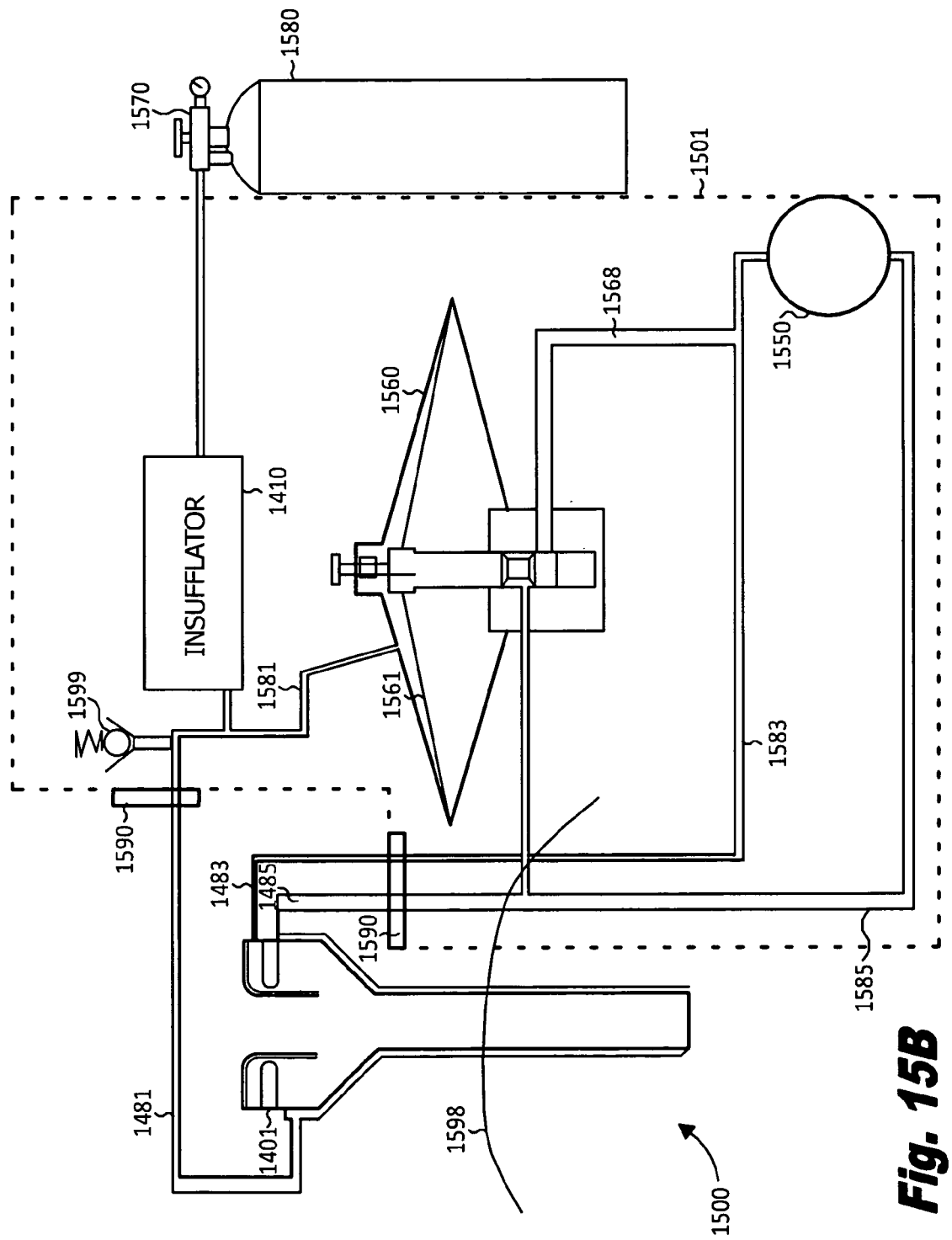
FIG. 15B is an alternate embodiment of the system of FIGS. 14 and 15A, including an integral pressure dumping valve.

FIG. 15B illustrates a system 1500, which is an alternate embodiment of the system 1400 of FIGS. 14 and 15A. The system 1500 is similar to system 1400, but simply additionally includes a safety pressure release valve 1599 in fluid connection with the pressure sensing line 1581. In cases of overpressure, in addition to the short-circuiting action of the pressure-controlled valve 1560, the safety pressure release valve 1599 can additionally release insufflation fluid into the atmosphere. The pressure setting at which the safety pressure release valve 1599 begins to release fluid can be set so that it does not prematurely release fluid, instead of the pressure-controlled valve 1560 recirculating fluid. Accordingly, the pressure setting may be slightly higher than for the pressure-controlled valve 1560.

With reference to FIG. 16, there is illustrated a control unit 1620 which is connected to an insufflating trocar 1401, both in accordance with the invention. A unitary filter element 1682 is provided, which is described in more detail below in connection with FIGS. 20-22. The control unit 1620 can be utilized with any embodiments of the systems described in accordance with the invention, and can include, as illustrated, a settable control 1621 for setting the desired pressure output from the control unit 1620, and a pressure gauge 1625 for confirming the set pressure. As illustrated, the filter 1682 mounts directly to the control unit 1620, with conduits integrally formed with the housing of the filter 1682 being received by corresponding apertures in the control unit 1620, as will be described in more detail below in connection with FIGS. 20-22. As with other embodiments set forth herein, the control unit 1620 can be connected with a standard surgical insufflator or can be provided with insufflator componentry within the housing of the control unit 1620.

FIGS. 17 and 18 illustrate an alternative embodiment of a system for surgical insufflation and gas recirculation 1700. As with the embodiment of FIGS. 14 and 15, an insufflator 1410 and control unit 1420 are each provided. However, the insufflator 1410 and control unit 1420 in this embodiment operate independently from one another, and each independently measures and responds to the abdominal pressure of the patient. As with the embodiment of FIGS. 14 and 15, the trocar having recirculation capability 1401 is connected by way of fluid conduits 1480 and filters 1482 to the control unit 1420. However, the insufflator 1410, instead of being connected to the control unit 1420, is connected by way of a fluid conduit 1780 to a secondary trocar 1701.

As shown in FIG. 18, insufflation gas is provided to the system 1700 from a supply, such as a tank 1580. In operation, when low abdominal pressure is sensed, the insufflator 1410 is triggered to insufflate the abdomen, and the pressure-controlled valve 1560 remains in a closed state, with the fluid pump 1550 receiving fluid from a return fluid plenum in the trocar 1401, through the return fluid conduit 1585, and delivering pressurized fluid through the fluid supply conduit 1583 to the nozzle of the trocar 1401.

When excessive abdominal pressure is experienced, the insufflator does not provide additional insufflation fluid to the abdomen, and the pressure-controlled valve 1560 opens, connecting the fluid supply conduit 1583 and the return fluid conduit 1585 through the bypass conduit 1568, thereby reducing the effectiveness of a fluid seal formed in the trocar 1401, and allowing a portion of the insufflation fluid to escape, and allowing the pressure within the abdominal cavity.

Figure 19:
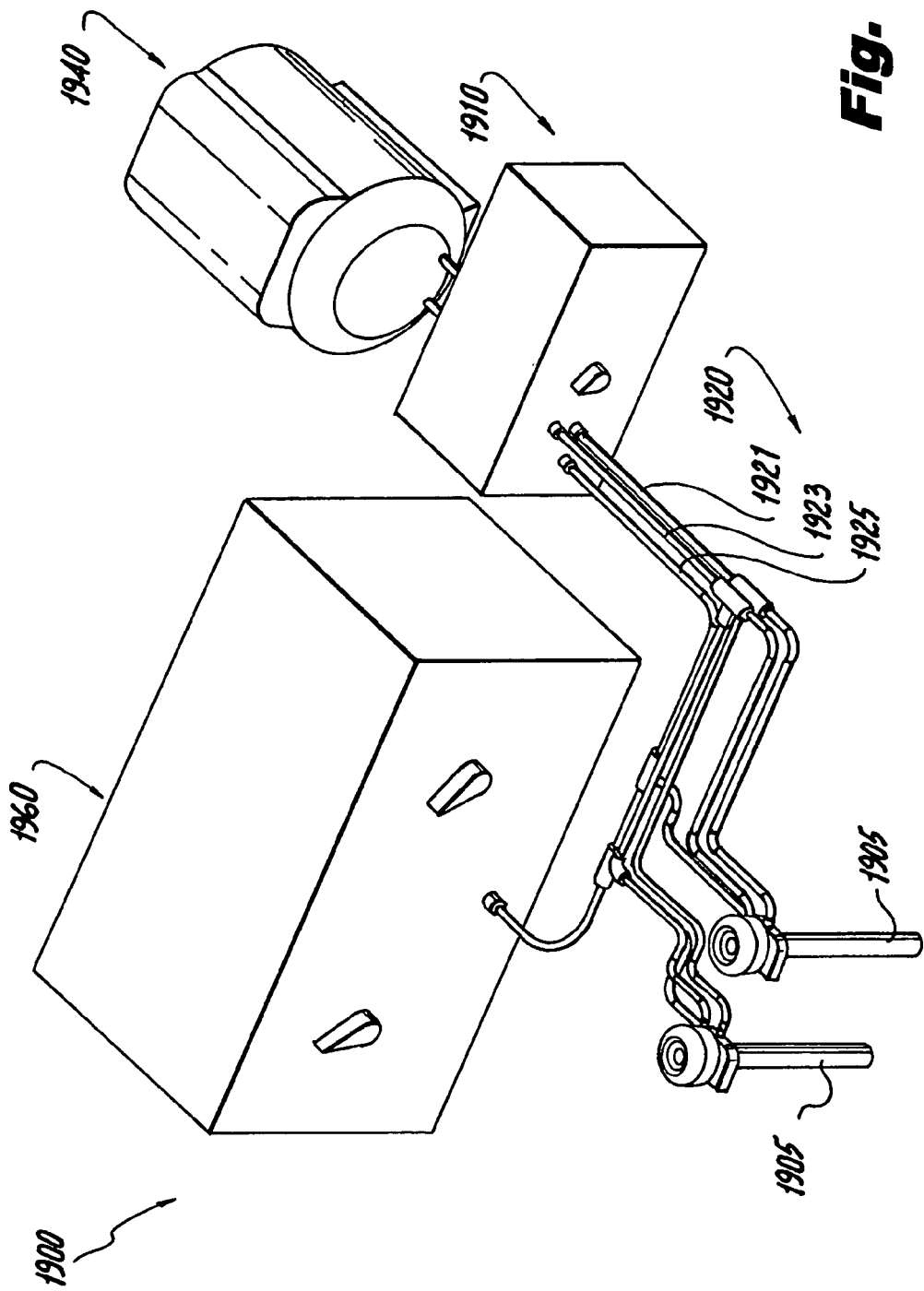
FIG. 19 is an isometric view of an alternate configuration of an insufflation and recirculation system in accordance with the invention.

With reference to FIG. 19, there is illustrated a system 1900 in accordance with the invention in which surgical access devices 1905 are connected via tubes 1920 to control equipment. In this case, control equipment includes an insufflator 1960, and a control unit 1910, which in turn is operably connected to a recirculation pump 1940, but which may include the pump 1940 within the housing of the control unit 1910.

In accordance with the invention, preferably all internal, gas contacting surfaces of the system, including tubing 1921, 1923, 1925 and portions of the recirculation pump 1940 are disposable. The pump 1940 may be of a peristaltic design, pumping gas by flexing disposable tubing, such as by a compressive roller system. Alternatively, pumping can be accomplished by external manipulation of a closed, integral and disposable diaphragm element. In accordance with the invention, it is preferred that wetted surfaces be disposed of after each procedure as a precautionary measure against cross-contamination. In alternate embodiments, systems in accordance with the invention can be provided with other types of fixed displacement pumps, or a variable displacement pump, such as vane pump, for example.

The surgical access devices 1905 are connected to the insufflator 1960 and control box 1910 by way of a pressure sense tube 1925. Pressurized fluid is delivered to the surgical access devices 1905 by way of a fluid supply tube 1921, while spent insufflation gas is retrieved by way of a return tube 1923, each tube being connected through a control unit 1910. One or more intervening filters can be disposed between the access devices 1905 and the control unit 1910, as illustrated in FIGS. 16 and 17.

A main fluid supply, such as a bottle of carbon dioxide gas, can be incorporated into the system 1900 in any suitable fashion, such as by providing an input in the control unit 1910, for example.

Figure 20:
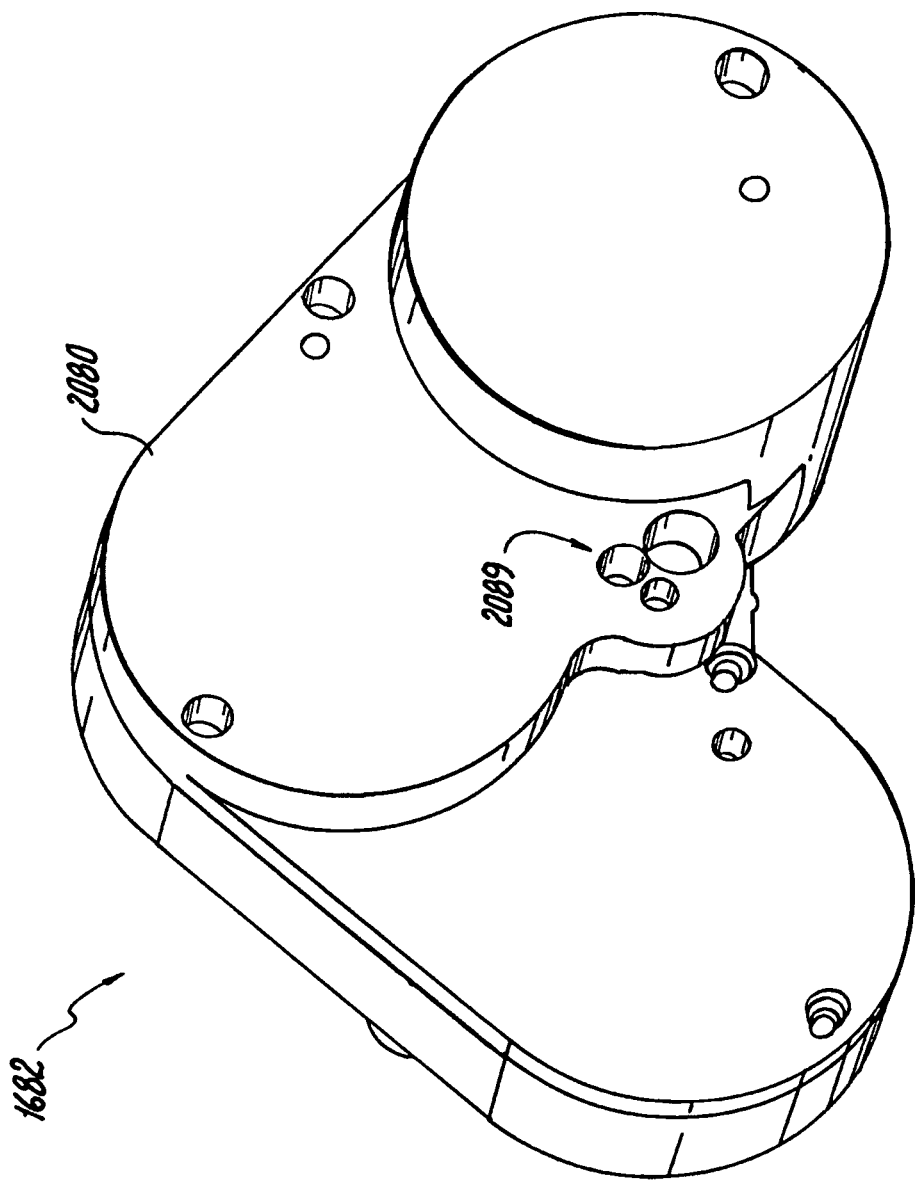
FIG. 20 is an isometric front view of a filter housing in accordance with the invention.
Figure 21:
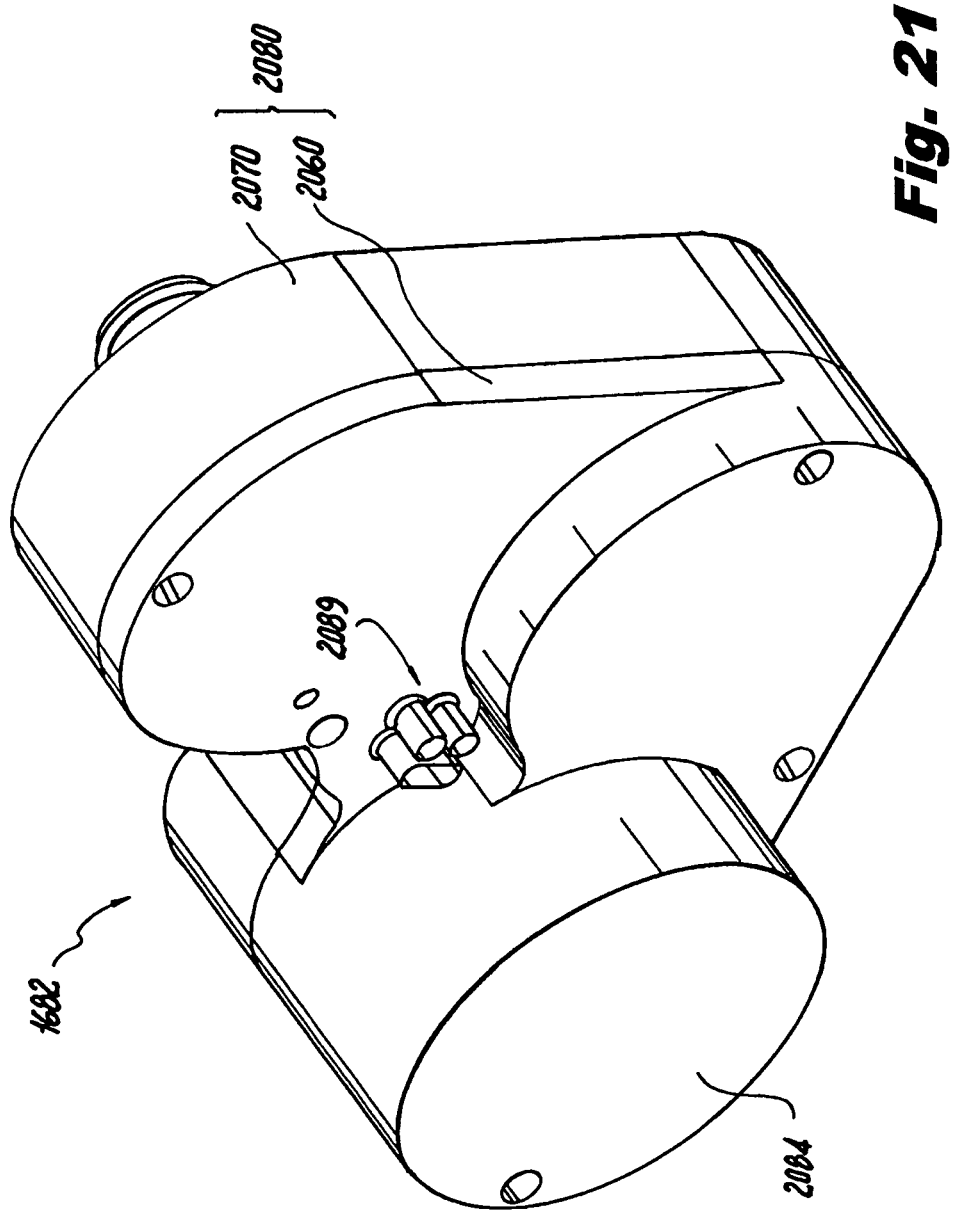
FIG. 21 is an isometric side view of the filter element of FIG. 20.
Figure 22:
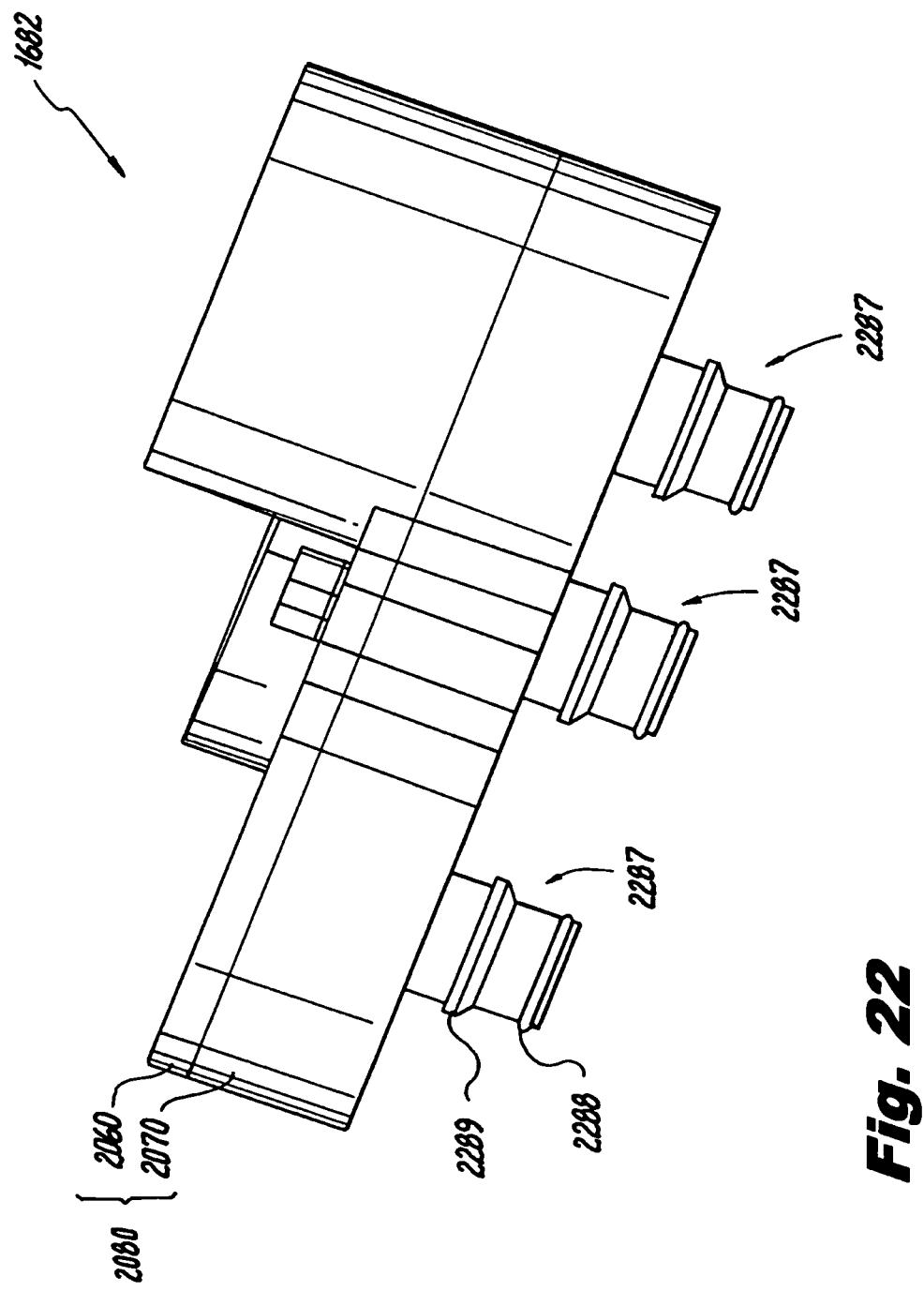
FIG. 22 is another isometric side view of the filter element of FIG. 20.
Figure 23:
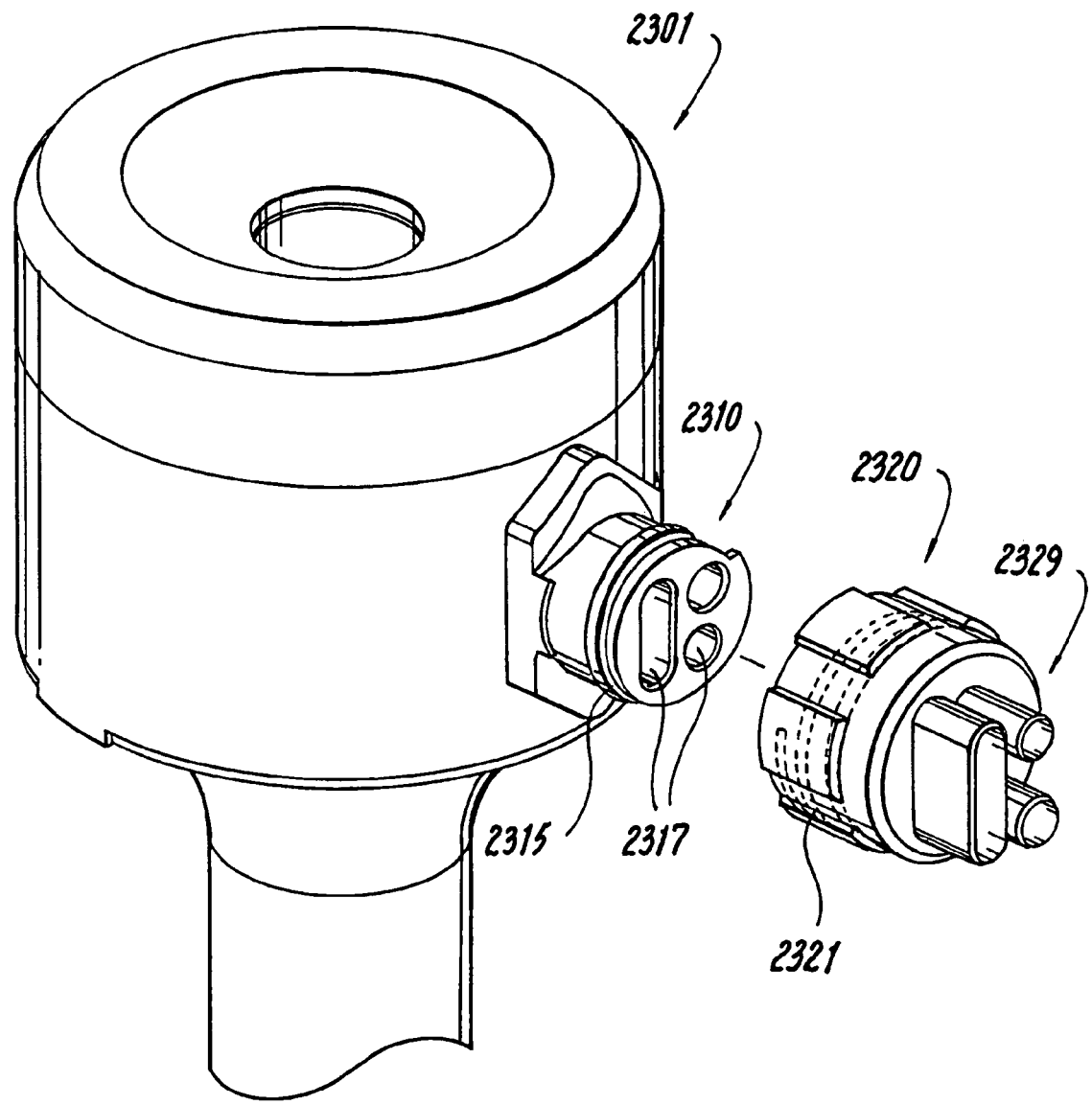
FIG. 23 is an isometric view of a connection between a tube set and a trocar, in accordance with the invention.
Figure 24:
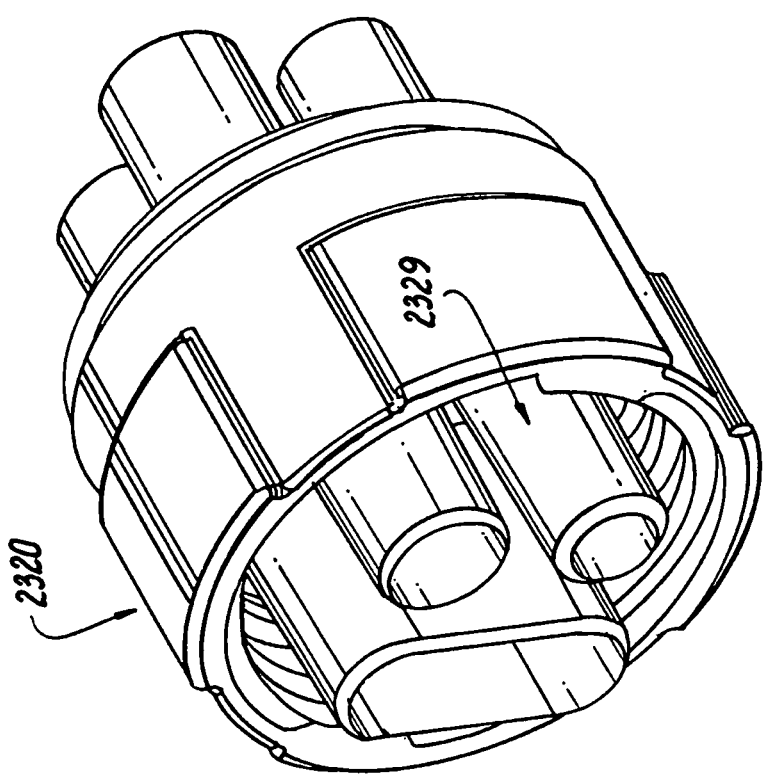
FIG. 24 is an isometric view of a tube end connector in accordance with the invention.
Figure 25:
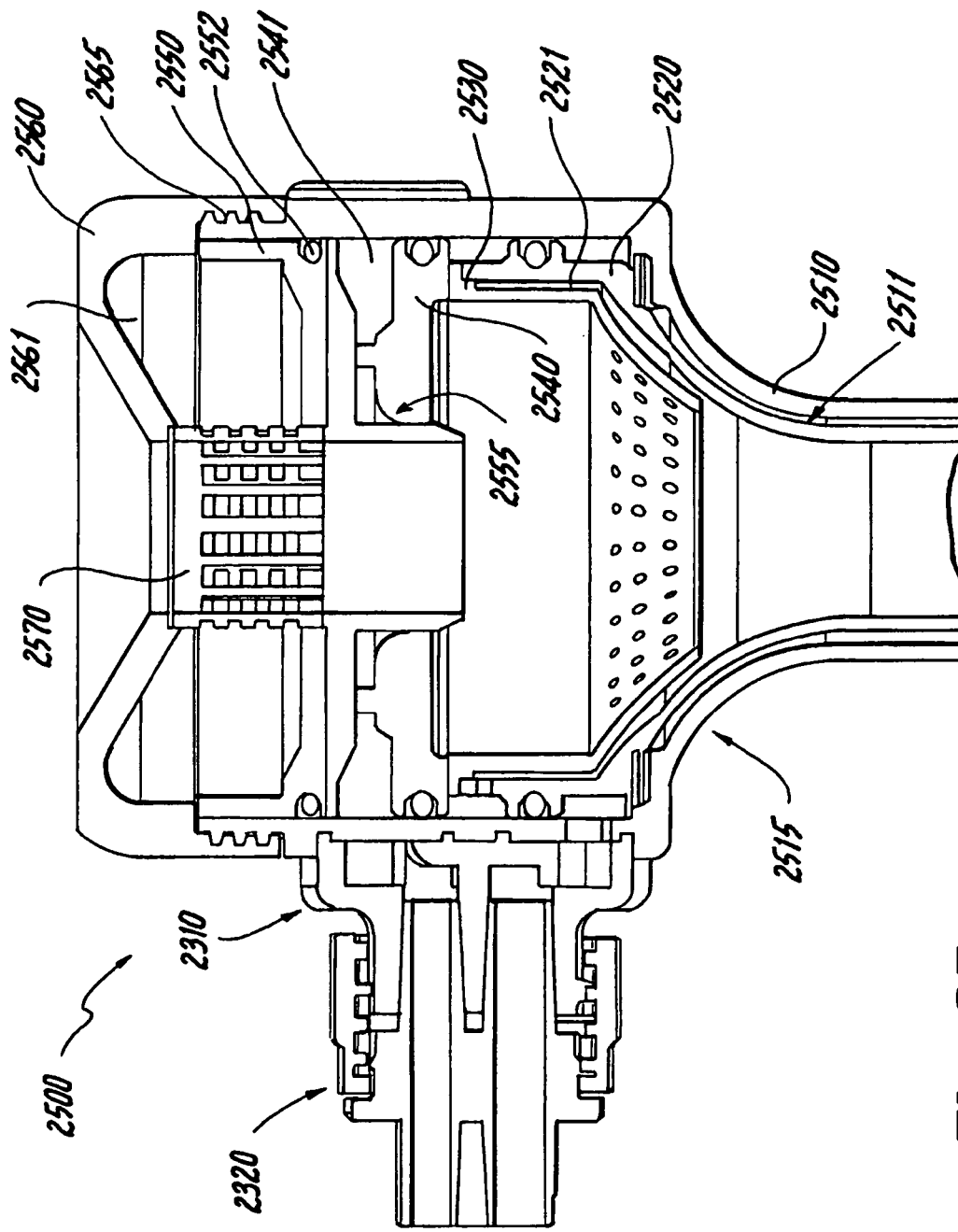
FIG. 25 is a cross-sectional view of a further embodiment of a trocar in accordance with the invention connected with a tube set.

Turning now to FIGS. 20-22, a filter assembly 1682 is illustrated. The filter assembly 1682 is provided with a housing 2080. The housing 2080 can be molded in two parts to simplify assembly, and can hold within it filter elements within separate, defined chambers corresponding to each of a fluid supply, fluid return and pressure sensing and/or insufflation conduit. Due to the different flow rates and pressures passing through each respective conduits, the filter size for that conduit is selected accordingly. As illustrated, particularly in FIG. 20, conduits 2089 are provided in the housing 2080, each in fluid communication with a fluid path and its respective filter element held within the housing 2080. The connection between the tubes and the filter 1682 can be any desired, and in accordance with the invention may be the same as the connection between the trocar and tube set, as illustrated in FIGS. 23-25, described in further detail below.

FIG. 21 is an isometric view of the filter 1682, illustrating the tube connection conduits 2089, and the parts 2060, 2070 that comprise the majority of the filter housing 2080. The front lid 2060, with conduits 2089 formed therein, is attached to the rear portion 2070, holding therewithin a plurality of filter elements for filtering fluid received from or provided to the trocar.

A fluid drain can be provided in one or more of the chambers defined within the housing 2080, particularly with the chamber 2084 corresponding to fluid returned from the trocar. Such drain can in turn, be connected to a central suction system to remove any collected fluid, or fluid can simply collect in the bottom of the housing 2080, or in a separate reservoir. As embodied, this chamber 2084 is preferably volumetrically larger than the other two chambers to accommodate a depressurized, and thus expanded flow of fluid returning from the trocar. The pressurized fluid being provided to the trocar takes up a proportionately lower volume, and accordingly, smaller filter chambers and tubes are sufficient to carry a given mass flow rate of insufflation fluid. When that same fluid is expanded upon its return, a larger conduit and filter chamber are necessary to handle the flow of fluid.

FIG. 22 is a side isometric view of the filter 1682, illustrating the rear conduits 2287 defined in the rear portion 2070 of the housing 2080. The conduits 2287 are configured to mate with corresponding apertures in a control unit, and include sealing elements 2288, such as O-rings, and protrusions 2289 for engaging a cooperating element in the housing to securely engage the filter 1682 to the control unit. Of course, the filter 1682 can be embodied such that instead of mounting on a control unit, the rear end of the filter connects to an intermediate tube set.

FIG. 23 illustrates two mating connection elements, including a boss 2310, and an end connector 2320 for connecting a trocar 2301 in accordance with the invention to a tube set (not illustrated in FIG. 23). The same connection arrangement can be used between the tube set and the filter, if so desired. A locking nut 2321 on the end connector 2320 engages an outer thread portion 2315 of the boss 2310, holding conduits 2329 securely to the trocar 2301. The conduits 2329, particularly on the end mating with the corresponding apertures 2317 formed in the boss 2310, can be formed of a compliant material such that they self-seal against the inner walls of respective apertures 2317. Alternatively or additionally, separate sealing elements can be utilized without departing from the spirit or scope of the invention. The general construction of the threaded engagement can be that of a "luer lock," is so-desired. FIG. 24 is an isometric view of the mating side of the end connector 2320.

FIG. 25 illustrates a trocar 2500 including a body 2510, having a housing 2515 arranged at the proximal end portion thereof. An annular insert 2540 and a nozzle insert 2550 define, in conjunction, a nozzle 2555 and a fluid supply plenum 2541. A fluid return plenum 2521 is defined between two inserts 2520 and 2530. Seals, 2552, such as O-rings can be provided in respective detents to seal between the inserts and the housing 2515. The nozzle insert 2550 is formed so as to have a depressed region which helps accommodate a proximal sound attenuation chamber 2561, in cooperation with a proximal cap 2560. Sound absorbing material can be provided in the sound attenuation chamber 2561 to help reduce noise emitted by the flowing fluid within the trocar 2500. A grating insert 2570 can be provided to help hold in and protect the sound attenuating material, and help further absorb excess sound.

The cap 2560, as illustrated, is adapted to threadedly engage the housing 2515 by way of mating threads 2565 formed on the housing 2515 and cap 2560. When assembled, screwing the cap 2560 to the housing 2515 causes all inserts to be firmly held within the housing 2515, providing for simple assembly of the trocar 2500.

The fluid return plenum 2521, fluid supply plenum 2541 and pressure sense and/or insufflation plenum 2511 are in fluid connection with respective conduits, which are connected through the connection boss 2310 provided on the housing 2515. The connection boss 2310, as described above, connects with a tube end connector 2320 to facilitate fluid supply to and removal from the trocar 2500.

Figure 26:
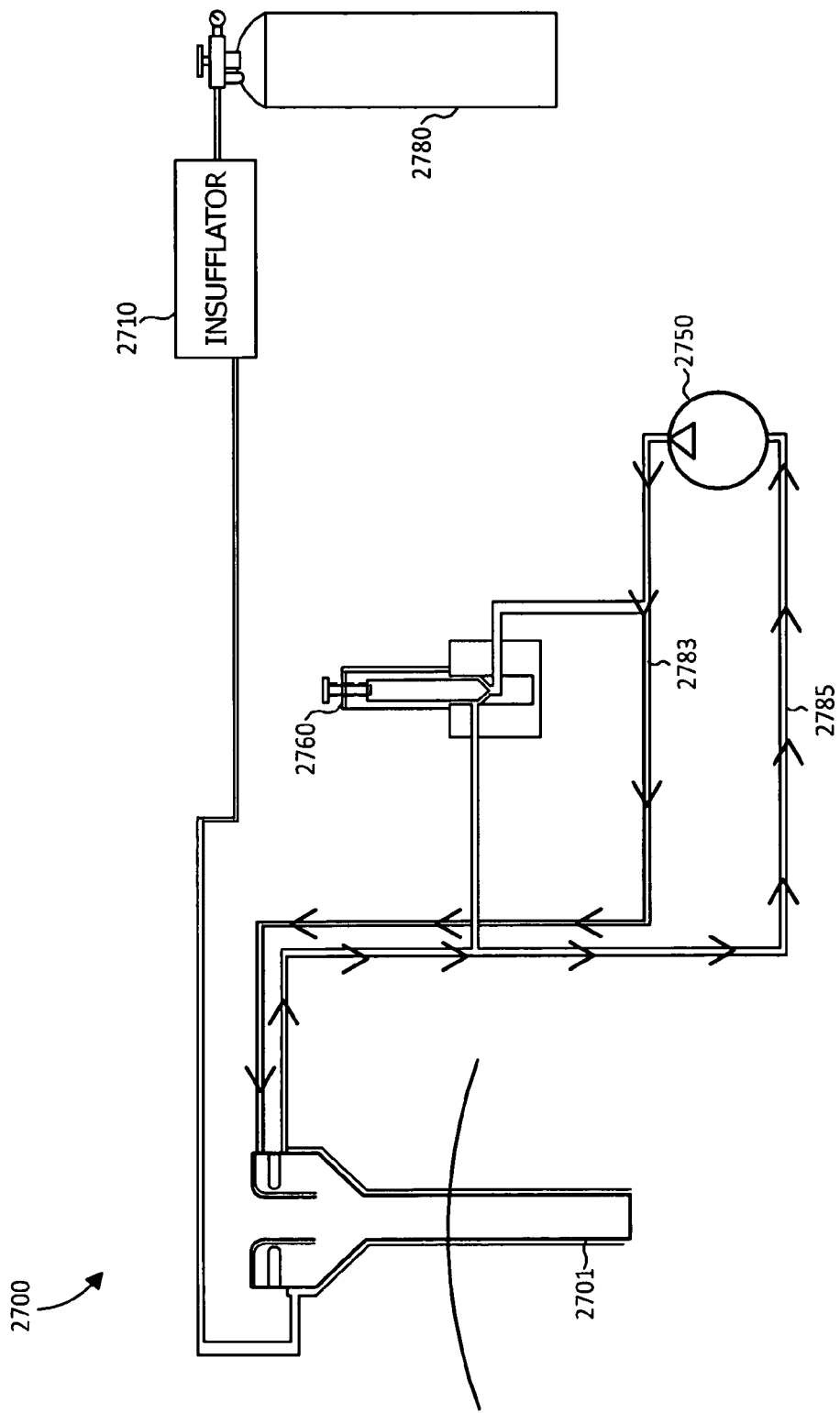
FIG. 26 is an alternate embodiment of an insufflation and recirculation system in accordance with the invention, having a back pressure control valve.
Figure 27:
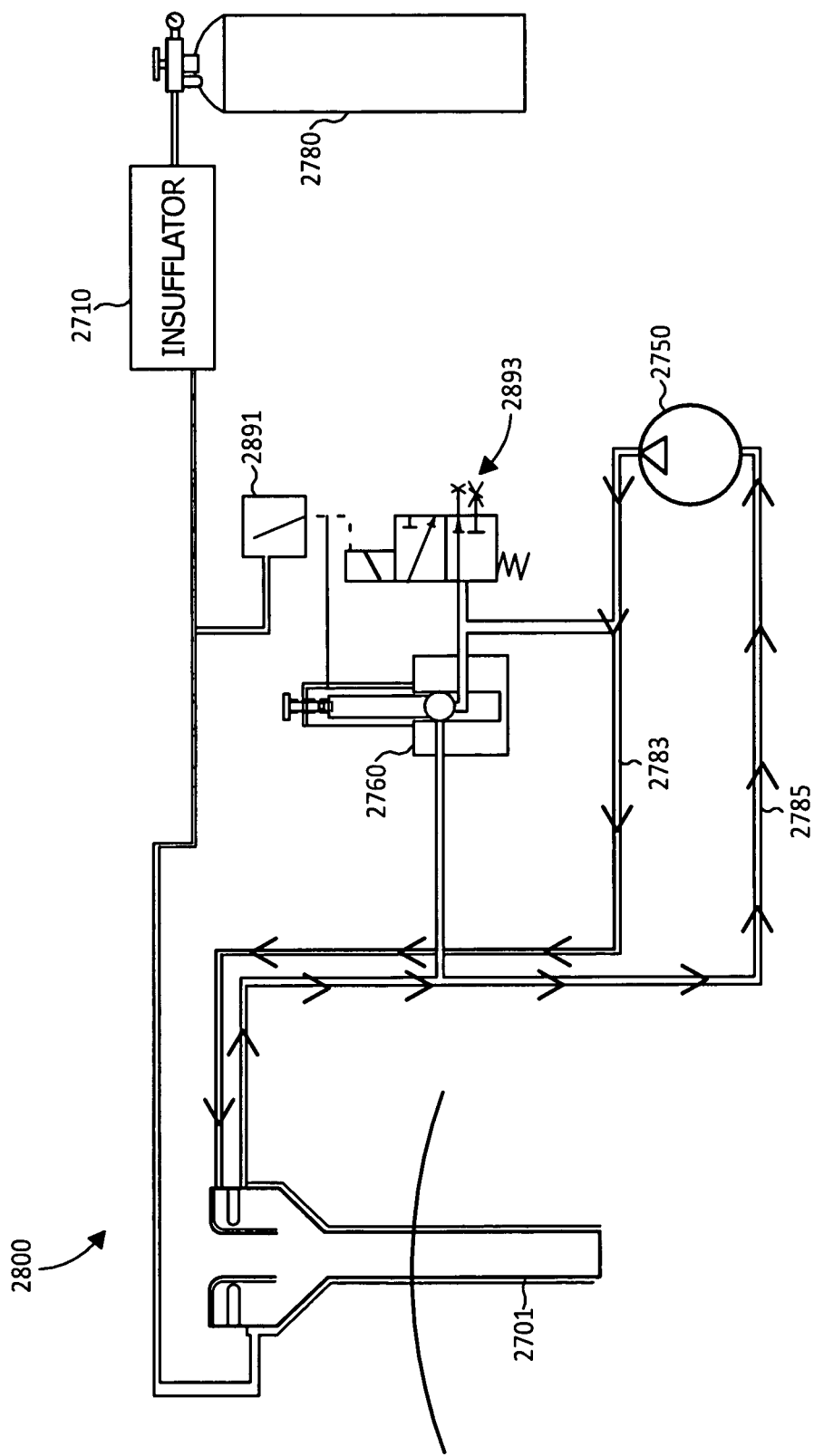
FIG. 27 is a further alternate embodiment of an insufflation and recirculation system in accordance with the invention, having a back pressure control valve, a pressure sensor and a pressure dump valve.

FIGS. 26 and 27 are schematic illustrations for alternate systems 2700, 2800 in accordance with the invention. The systems 2700, 2800 of FIGS. 26 and 27, can be incorporated integrally with a surgical insufflator similar to the embodiments of FIGS. 15A and 15B, or may be independent of a surgical insufflator like the embodiment of FIGS. 17 and 18, with the insufflator 1410 and control unit 1420 operating independently from one another, and each independently measuring and responding to the abdominal pressure of the patient.

In each embodiment, the trocar having recirculation capability 2701 is connected to an insufflator 2710, a pump 2750 and a valve. In the embodiment of FIG. 26, the valve 2760 is a back pressure control valve, which permits pressure on the upstream side of the valve 2760 only up to a certain preset value. When pressure in the supply conduit 2783 exceeds the set value, it short-circuits to the return line 2785. This lowers the supply pressure and reduces or shuts off the fluid seal created by the pressurized flow entering the trocar 2701, thereby allowing insufflation fluid in the abdominal cavity to escape through the lumen of the trocar 2701. Because the lumen of the trocar can be relatively large, such pressure can escape quickly, thereby preventing any harm to the patient. Because the fluid is recirculated in the valve, a minimum of insufflation gas is wasted by dissipating it into the atmosphere.

The system 2800 of FIG. 27 includes an additional dump valve 2893 in connection with the fluid supply conduit 2783. In addition to the short-circuiting action of the pressure valve 2860 described above, the system 2800 is provided with a pressure sensor 2891, which can be mechanical but is, as illustrated, electronic. The pressure sensor 2891 can be in fluid communication with the insufflation line or other source of abdominal pressure. When an over-pressure condition is sensed, the pressure sensor 2891 signals the dump valve 2893 to release fluid out of the system. As illustrated, the dump valve 2893 is electro-mechanical, but alternatively may be fully mechanical, as desired.

The devices, systems and methods of the present invention, as described above and shown in the drawings, provide for advantageous systems for surgical insufflation and gas recirculation, and related devices and methods therefor. It will be apparent to those skilled in the art that various modifications and variations can be made in the devices, systems and methods of the present invention without departing from the spirit or scope of the invention. Thus, it is intended that the present invention include such modifications and variations that are within the scope of the appended claims and their equivalents.

What is claimed is:

1. A system for insufflation and recirculation of pressurized fluid in a surgical procedure, the system comprising:
a control unit having:
 a) a fluid pump adapted and configured to circulate pressurized fluid during the surgical procedure;
 b) a supply conduit in fluid communication with an output of the fluid pump for delivering pressurized fluid to an output port of the control unit;
 c) a return conduit in fluid communication with an input of the fluid pump for returning fluid from an input port of the control unit;
 d) a valve assembly in fluid communication with the supply conduit and the return conduit, the valve assembly remaining in a closed state in the absence of a control signal corresponding to a change in abdominal pressure and being adapted and configured to respond to a sensed overpressure condition by opening an internal flow path, thereby fluidly connecting the supply conduit and the return conduit with one another;
 e) a pressure sensing conduit in fluid communication with the valve assembly for communicating a pressure value thereto;
 f) a safety pressure release valve in fluid communication with the pressure sensing conduit for releasing pressurized fluid into the atmosphere in addition to the opening of the internal flow path of the valve assembly; and
a surgical insufflator configured to receive, through an input port thereof, a supply of insufflation gas from a source, wherein an output port of the insufflator is in fluid communication with a patient's abdominal cavity, and the insufflator is further configured to sense pressure within the abdominal cavity by way of the pressure sensing conduit and provide insufflation gas to the abdominal cavity through the pressure sensing conduit.

2. The system as recited in claim 1, wherein the control unit and the surgical insufflator are contained in a single housing.

3. The system as recited in claim 1, further comprising a trocar coupled to the control unit and including:
 a) a body having a lumen extending therethrough;
 b) a nozzle within the body for directing pressurized fluid into the lumen;
 c) a fluid return plenum configured to collect spent insufflation fluid;
 d) a fluid supply port in fluid communication with the nozzle for delivering a pressurized flow of fluid to the nozzle and configured to receive pressurized fluid from the output port of the control unit; and
 e) a fluid return port in fluid communication with the fluid return plenum and configured to return spent insufflation fluid from the trocar to the input port of the control unit.

4. The system as recited in claim 3, wherein the trocar further comprises a pressure sensing chamber in fluid communication with the patient's abdominal cavity and with the valve assembly of the control unit through the pressure sensing conduit.

5. The system as recited in claim 1, wherein the safety pressure release valve is configured to release pressurized fluid into the atmosphere at a sensed pressure that is higher than the sensed pressure at which the internal flow path of the valve assembly opens to fluidly connect the supply conduit and the return conduit with one another.

6. A system for insufflation and recirculation of pressurized fluid in a surgical procedure, the system comprising:
a control unit having:
 a) a fluid pump adapted and configured to circulate pressurized fluid and maintain a fluid seal within a trocar coupled to the control unit;

b) a supply conduit in fluid communication with an output of the fluid pump and configured and adapted for delivering pressurized fluid to an output port of the control unit;

c) a return conduit in fluid communication with an input of the fluid pump for returning fluid from an input port of the control unit;

d) a valve assembly in fluid communication with the supply conduit and the return conduit, the valve assembly remaining in a closed state in the absence of a control signal corresponding to a change in abdominal pressure and being adapted and configured to respond to a sensed overpressure condition by opening an internal flow path, thereby fluidly connecting the supply conduit and the return conduit with one another through a bypass conduit, to reduce the supply of fluid to the fluid seal within the trocar;

e) a pressure sensing conduit in fluid communication with the valve assembly to communicate a pressure value thereto;

f) a safety pressure release valve in fluid communication with the pressure sense conduit for releasing pressurized fluid into the atmosphere in addition to the opening of the internal flow path of the valve assembly; and a surgical insufflator configured to receive, through an input port thereof, a supply of insufflation gas from a source, wherein an output port of the insufflator is in fluid communication with a patient's abdominal cavity by way of the trocar, and the insufflator is further configured to sense pressure within the abdominal cavity by way of the pressure sensing conduit and provide insufflation gas to the abdominal cavity through the pressure sense conduit.

7. The system as recited in claim 6, wherein the control unit and the surgical insufflator are contained in a single housing.

8. The system as recited in claim 6, wherein the trocar includes:
   a) a body having a lumen extending therethrough;
   b) a nozzle within the body for directing pressurized fluid into the lumen;
   c) a fluid return plenum configured to collect spent insufflation fluid;
   d) a supply port in fluid communication with the nozzle for delivering a pressurized flow of fluid to the nozzle and configured to receive pressurized fluid from the output port of the control unit; and
   e) a fluid return port in fluid communication with the fluid return plenum and configured to return spent insufflation fluid from the trocar to the input port of the control unit.

9. The system as recited in claim 8, wherein the trocar further comprises a pressure sensing chamber in fluid communication with the patient's abdominal cavity and with the valve assembly of the control unit through the pressure sensing conduit.

10. The system as recited in claim 6, wherein the safety pressure release valve is configured to release pressurized fluid into the atmosphere at a sensed pressure that is higher than the sensed pressure at which the internal flow path of the valve assembly opens to fluidly connect
   the supply conduit and the return conduit with one another through the bypass conduit.

* * * * *